(12) United States Patent
Murray et al.

(10) Patent No.: US 6,972,294 B1
(45) Date of Patent: Dec. 6, 2005

(54) COMPOUNDS, THEIR PREPARATION AND USE

(75) Inventors: Anthony Murray, Hellerup (DK); Per Sauerberg, Farum (DK); Lone Jeppesen, Virum (DK); Ingrid Pettersson, Frederiksberg (DK); Paul Stanley Bury, København (DK)

(73) Assignee: Novo Nordisk, A/S, Bagsvaerd (DK)

( * ) Notice: Subject to any disclaimer, the term of this patent is extended or adjusted under 35 U.S.C. 154(b) by 0 days.

(21) Appl. No.: 09/551,740

(22) Filed: Apr. 18, 2000

Related U.S. Application Data

(60) Provisional application No. 60/132,193, filed on May 3, 1999.

(30) Foreign Application Priority Data

Apr. 20, 1999 (DK) ................................ 1999 00533

(51) Int. Cl.[7] .................... C07D 213/02; A61K 31/44
(52) U.S. Cl. ................ 514/345; 514/438; 514/461; 514/530; 514/532; 514/533; 514/570; 546/301; 548/79; 548/499; 548/500; 560/9; 560/57; 562/468
(58) Field of Search ................... 568/491; 514/543, 514/345, 438, 461, 530, 532, 533, 570; 546/301; 548/79, 499, 500; 560/9, 57; 562/468

(56) References Cited

U.S. PATENT DOCUMENTS 5,306,726 A    4/1994    Hulin ................. 514/375

FOREIGN PATENT DOCUMENTS

| EP | 0623605 A | * 4/1994 |
| EP | 0 903 343 | 3/1999 |
| WO | 91/19702 | 12/1991 |
| WO | 94/01420 | 1/1994 |
| WO | 94/13650 | 6/1994 |
| WO | 95/03038 | 1/1995 |
| WO | 95/17394 | 6/1995 |
| WO | 96/04620 | 2/1996 |
| WO | WO 96/04261 | 2/1996 |
| WO | WO 97/25042 | 7/1997 |
| WO | WO 97/31907 | 9/1997 |
| WO | 97/36579 | 10/1997 |
| WO | WO 99/08501 | 2/1999 |
| WO | WO 99/16758 | 4/1999 |
| WO | WO 99/19313 | 4/1999 |
| WO | WO 99/20614 | 4/1999 |
| WO | WO 99/38850 | 8/1999 |

OTHER PUBLICATIONS

CAPLUS accession No. 1998:430714, Japanese Abstract No. JP 10182550.

* cited by examiner

*Primary Examiner*—Zinna Northington Davis
(74) *Attorney, Agent, or Firm*—Rosemarie R. Wilk-Orescan; Reza Green; Richard W. Book

(57) ABSTRACT

Disclosed are novel compounds of formula (I)

$$A^1\underset{\underset{(CH_k)}{\|}}{\overset{Z}{\diagdown}}A^2$$

wherein $A^1$, $A^2$, Ar, $R^5$, $R^6$, $R^8$, M, Q, Y, Z, k, m and n are as defined in the specification. These compounds are useful in the treatment and/or prevention of conditions mediated by nuclear receptors, in particular the Peroxisome Proliferator-Activated Receptors (PPAR). Such conditions include diabetes and obesity.

17 Claims, No Drawings

COMPOUNDS, THEIR PREPARATION AND USE

CROSS-REFERENCES TO RELATED APPLICATIONS

The present invention claims priority under 35 U.S.C. 119 of U.S. provisional application No. 60/132,193 filed May 3, 1999 and Danish application no. PA 1999 00533 filed Apr. 20, 1999, the contents of which are fully incorporated herein by reference.

BACKGROUND OF THE INVENTION

1. Field of the Invention

The present invention relates to novel compounds, pharmaceutical compositions containing them, methods for preparing the compounds and their use as medicaments. More specifically, compounds of the invention can be utilized in the treatment and/or prevention of conditions mediated by nuclear receptors, in particular the Peroxisome Proliferator-Activated Receptors (PPAR).

2. Description of the Related Art

Coronary artery disease (CAD) is the major cause of death in Type 2 diabetic and metabolic syndrome patients (i.e. patients that fall within the 'deadly quartet' category of impaired glucose tolerance, insulin resistance, hypertriglyceridemia and/or obesity).

The hypolipidemic fibrates and antidiabetic thiazolidinediones separately display moderately effective triglyceride-lowering activities although they are neither potent nor efficacious enough to be a single therapy of choice for the dyslipidemia often observed in Type 2 diabetic or metabolic syndrome patients. The thiazolidinediones also potently lower circulating glucose levels of Type 2 diabetic animal models and humans. However, the fibrate class of compounds are without beneficial effects on glycemia. Studies on the molecular actions of these compounds indicate that thiazolidinediones and fibrates exert their action by activating distinct transcription factors of the peroxisome proliferator-activated receptor (PPAR) family, resulting in increased and decreased expression of specific enzymes and apolipoproteins respectively, both key players in regulation of plasma triglyceride content. Fibrates, on the one hand, are PPARα activators, acting primarily in the liver. Thiazolidinediones, on the other hand, are high affinity ligands for PPARγ acting primarily on adipose tissue.

Adipose tissue plays a central role in lipid homeostasis and the maintenance of energy balance in vertebrates. Adipocytes store energy in the form of triglycerides during periods of nutritional affluence and release it in the form of free fatty acids at times of nutritional deprivation. The development of white adipose tissue is the result of a continuous differentiation process throughout life. Much evidence points to the central role of PPARγ activation in initiating and regulating this cell differentiation. Several highly specialized proteins are induced during adipocyte differentiation, most of them being involved in lipid storage and metabolism. The exact link from activation of PPARγ to changes in glucose metabolism, most notably a decrease in insulin resistance in muscle, has not yet been clarified. A possible link is via free fatty acids such that activation of PPARγ induces Lipoprotein Lipase (LPL), Fatty Acid Transport Protein (FATP) and Acyl-CoA Synthetase (ACS) in adipose tissue but not in muscle tissue. This, in turn, reduces the concentration of free fatty acids in plasma dramatically, and due to substrate competition at the cellular level, skeletal muscle and other tissues with high metabolic rates eventually switch from fatty acid oxidation to glucose oxidation with decreased insulin resistance as a consequence.

PPARα is involved in stimulating β-oxidation of fatty acids. In rodents, a PPARα-mediated change in the expression of genes involved in fatty acid metabolism lies at the basis of the phenomenon of peroxisome proliferation, a pleiotropic cellular response, mainly limited to liver and kidney and which can lead to hepatocarcinogenesis in rodents. The phenomenon of peroxisome proliferation is not seen in man. In addition to its role in peroxisome proliferation in rodents, PPARα is also involved in the control of HDL cholesterol levels in rodents and humans. This effect is, at least partially, based on a PPARα-mediated transcriptional regulation of the major HDL apolipoproteins, apo A-I and apo A-II. The hypotriglyceridemic action of fibrates and fatty acids also involves PPARα and can be summarized as follows: (I) an increased lipolysis and clearance of remnant particles, due to changes in lipoprotein lipase and apo C-III levels, (II) a stimulation of cellular fatty acid uptake and their subsequent conversion to acyl-CoA derivatives by the induction of fatty acid binding protein and acyl-CoA synthase, (III) an induction of fatty acid oxidation pathways, (IV) a reduction in fatty acid and triglyceride synthesis, and finally (V) a decrease in VLDL production. Hence, both enhanced catabolism of triglyceride-rich particles as well as reduced secretion of VLDL particles constitutes mechanisms that contribute to the hypolipidemic effect of fibrates.

A number of compounds have been reported to be useful in the treatment of hyperglycemia, hyperlipidemia and hypercholesterolemia (U.S. Pat. No. 5,306,726, PCT Publications nos. WO91/19702, WO 95/03038, WO 96/04260, WO 94/13650, WO 94/01420, WO 97/36579, WO 97/25042, WO 95/17394, WO 99/08501, WO 99/19313 and WO 99/16758).

SUMMARY OF THE INVENTION

Glucose lowering as a single approach does not overcome the macrovascular complications associated with Type 2 diabetes and metabolic syndrome. Novel treatments of Type 2 diabetes and metabolic syndrome must therefore aim at lowering both the overt hypertriglyceridemia associated with these syndromes as well as alleviation of hyperglycemia.

The clinical activity of fibrates and thiazolidinediones indicates that research for compounds displaying combined PPARα and PPARγ activation should lead to the discovery of efficacious glucose and triglyceride lowering drugs that have great potential in the treatment of Type 2 diabetes and the metabolic syndrome (i.e. impaired glucose tolerance, insulin resistance, hypertriglyceridemia and/or obesity).

DETAILED DESCRIPTION OF THE INVENTION

Accordingly, the present invention relates to compounds of formula (I):

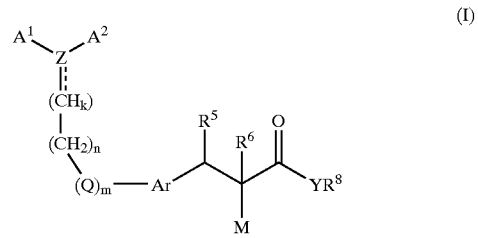

wherein $A^1$ and $A^2$ are independently of each other a 5–6 membered cyclic ring or a 9–10 membered bicyclic ring, optionally substituted with one or more halogen, perhalomethyl, hydroxy, nitro, cyano, formyl, or $C_{1\text{-}12}$-alkyl, $(C_{3\text{-}6}$-cycloalkyl$)C_{1\text{-}6}$-alkyl, $C_{4\text{-}12}$-alkenynyl, $C_{2\text{-}12}$-alkenyl, $C_{2\text{-}12}$-alkynyl, $C_{1\text{-}12}$-alkoxy, aryl, aryloxy, arylalkyl, arylalkoxy, heterocyclyl, heteroaryl, heteroarylalkyl, heteroaryloxy, heteroarylalkoxy, acyl, acyloxy, hydroxy$C_{1\text{-}12}$-alkyl, amino, acylamino, $C_{1\text{-}12}$-alkyl-amino, $C_{1\text{-}6}$-dialkylamino, arylamino, arylalkylamino, amino$C_{1\text{-}12}$-alkyl, $C_{1\text{-}12}$-alkoxycarbonyl, alkylaminocarbonyl, aryloxycarbonyl, arylalkoxycarbonyl, $C_{1\text{-}12}$-alkoxy$C_{1\text{-}12}$-alkyl, aryloxy$C_{1\text{-}12}$-alkyl, arylalkoxy$C_{1\text{-}12}$-alkyl, arylthio, $C_{1\text{-}12}$-alkylthio, thio$C_{1\text{-}12}$-alkyl, $C_{1\text{-}12}$alkoxycarbonylamino, aryloxycarbonylamino, arylalkoxycarbonylamino, —$COR^1$, or —$SO_2R^2$, wherein $R^1$ and $R^2$ independently of each other are selected from hydroxy, halogen, perhalomethyl, $C_{1\text{-}6}$-alkoxy or amino optionally substituted with one or more $C_{1\text{-}6}$-alkyl, perhalomethyl or aryl; optionally substituted with one or more halogen, perhalomethyl, hydroxy, nitro or cyano;

Z is C or $CR^3$, wherein $R^3$ is hydrogen, halogen, perhalomethyl, $C_{1\text{-}12}$-alkyl, $C_{4\text{-}12}$alkenynyl, $C_{2\text{-}12}$-alkenyl, $C_{2\text{-}12}$-alkynyl, $C_{1\text{-}12}$-alkoxy, aryloxy, arylalkoxy, heteroaryloxy, heteroarylalkoxy, acyl, acyloxy, hydroxy$C_{1\text{-}12}$-alkyl, $C_{1\text{-}12}$-alkoxy$C_{1\text{-}12}$-alkyl, aryloxy$C_{1\text{-}12}$-alkyl, arylalkoxy$C_{1\text{-}12}$-alkyl, thio$C_{1\text{-}12}$-alkyl, —$COR^4$, or —$SO_2R^4$, wherein $R^4$ and $R^{11}$ independently of each other are selected from hydroxy, halogen, perhalomethyl, $C_{1\text{-}6}$-alkoxy or amino optionally substituted with one or more $C_{1\text{-}6}$-alkyl, perhalomethyl or aryl optionally substituted with one or more halogen, perhalomethyl, hydroxy, nitro or cyano;

Q is O, S or $NR^{12}$, wherein $R^{12}$ is hydrogen, perhalomethyl, $C_{1\text{-}12}$-alkyl, $C_{4\text{-}12}$alkenynyl, $C_{2\text{-}12}$-alkenyl, $C_{2\text{-}12}$-alkynyl, aryl, arylalkyl, heterocyclyl, heteroaryl, heteroarylalkyl, acyl, hydroxy$C_{1\text{-}12}$-alkyl, amino$C_{1\text{-}12}$-alkyl, $C_{1\text{-}12}$-alkoxycarbonyl, aryloxycarbonyl, arylalkoxycarbonyl, $C_{1\text{-}12}$-alkoxy$C_{1\text{-}12}$-alkyl, aryloxy$C_{1\text{-}12}$-alkyl, arylalkoxy$C_{1\text{-}12}$-alkyl, thio$C_{1\text{-}12}$-alkyl, —$COR^{13}$, or —$SO_2R^{14}$, wherein $R^{13}$ and $R^{14}$ independently of each other are selected from hydroxy, perhalomethyl, $C_{1\text{-}6}$-alkoxy or amino optionally substituted with one or more $C_{1\text{-}6}$-alkyl, perhalomethyl or aryl optionally substituted with one or more halogen, perhalomethyl, hydroxy, nitro or cyano;

----- represents a single bond or a double bond;

Ar represents arylene, heteroarylene, or a divalent heterocyclic group each of which can optionally be substituted with one or more halogen, $C_{1\text{-}6}$-alkyl, amino, hydroxy, $C_{1\text{-}6}$-alkoxy or aryl;

$R^5$ represents hydrogen, hydroxy, halogen, $C_{1\text{-}12}$-alkoxy, $C_{1\text{-}12}$-alkyl, $C_{4\text{-}12}$-alkenynyl, $C_{2\text{-}12}$alkenyl, $C_{2\text{-}12}$-alkynyl or arylalkyl; optionally substituted with one or more halogen, perhalomethyl, hydroxy, nitro or cyano or $R^5$ forms a bond together with $R^6$;

$R^6$ represents hydrogen, hydroxy, halogen, $C_{1\text{-}12}$-alkoxy, $C_{1\text{-}12}$-alkyl, $C_{4\text{-}12}$-alkenynyl, $C_{2\text{-}12}$-alkenyl, $C_{2\text{-}12}$-alkynyl, acyl or arylalkyl optionally substituted with one or more halogen, perhalomethyl, hydroxy, nitro or cyano or $R^6$ forms a bond together with $R^5$;

M represents $OR^7$, where $R^7$ represents hydrogen, $C_{1\text{-}12}$-alkyl, $C_{4\text{-}12}$-alkenynyl, $C_{2\text{-}12}$-alkenyl, $C_{2\text{-}12}$-alkynyl, aryl, arylalkyl, $C_{1\text{-}12}$-alkoxy$C_{1\text{-}12}$-alkyl, $C_{1\text{-}12}$-alkoxycarbonyl, aryloxycarbonyl, $C_{1\text{-}12}$-alkylaminocarbonyl, arylaminocarbonyl, acyl, heterocyclyl, heteroaryl or heteroarylalkyl groups optionally substituted with one or more halogen, perhalomethyl, hydroxy, nitro or cyano or M represents $COYR^6$;

$R^8$ represents hydrogen, $C_{1\text{-}12}$alkyl, $C_{4\text{-}12}$-alkenynyl, $C_{2\text{-}12}$-alkenyl, $C_{2\text{-}12}$-alkynyl, aryl, arylalkyl, heterocyclyl, heteroaryl or heteroarylalkyl groups optionally substituted with one or more halogen, perhalomethyl, hydroxy, nitro or cyano;

Y represents oxygen, sulphur or $NR^{10}$, where $R^{10}$ represents hydrogen, $C_{1\text{-}12}$-alkyl, aryl, hydroxy$C_{1\text{-}12}$-alkyl or arylalkyl groups or when Y is $NR^{10}$, $R^8$ and $R^{10}$ may form a 5 or 6 membered nitrogen containing ring, optionally substituted with one or more $C_{1\text{-}6}$-alkyl;

k is an integer ranging from 1 to 2, n is an integer ranging from 0 to 3 and m is an integer ranging from 0 to 1;

or a salt thereof with a pharmaceutically acceptable acid or base, or any optical isomer or mixture of optical isomers, including a racemic mixture, or any tautomeric forms.

In a preferred embodiment, the present invention is concerned with compounds of formula I wherein $A^1$ and $A^2$ are independently of each other a 5–6 membered cyclic ring or a 9–10 membered bicyclic ring, optionally substituted with one or more halogen, perhalomethyl, hydroxy, $C_{1\text{-}6}$-alkyl, $(C_{3\text{-}6}$-cycloalkyl$)C_{1\text{-}6}$-alkyl, $C_{4\text{-}6}$-alkenynyl, $C_{2\text{-}6}$-alkenyl, $C_{2\text{-}6}$-alkynyl, $C_{1\text{-}6}$-alkoxy, aryl, aryloxy, arylalkyl, arylalkoxy, heterocyclyl, heteroaryl, heteroarylalkyl, heteroaryloxy, heteroarylalkoxy, acyl, hydroxy$C_{1\text{-}6}$-alkyl, $C_{1\text{-}6}$-alkylamino, $C_{1\text{-}6}$-dialkylamino, arylamino, arylalkylamino, amino$C_{1\text{-}6}$-alkyl, $C_{1\text{-}6}$-alkoxycarbonyl, alkylaminocarbonyl, aryloxycarbonyl, arylalkoxycarbonyl, $C_{1\text{-}6}$alkoxy$C_{1\text{-}6}$-alkyl, aryloxy$C_{1\text{-}6}$-alkyl, or arylalkoxy$C_{1\text{-}6}$-alkyl.

In another preferred embodiment, the present invention is concerned with compounds of formula I wherein $A^1$ and $A^2$ are independently of each other a 5–6 membered cyclic ring or a 9–10 membered bicyclic ring, optionally substituted with one or more halogen, perhalomethyl, hydroxy, $C_{1\text{-}6}$-alkyl, $(C_{3\text{-}6}$-cycloalkyl$)C_{1\text{-}6}$-alkyl, $C_{4\text{-}6}$-alkenynyl, $C_{2\text{-}6}$-alkenyl, $C_{2\text{-}6}$-alkynyl, $C_{2\text{-}6}$-alkoxy, aryl, aryloxy, arylalkyl, arylalkoxy, heterocyclyl, heteroaryl, heteroarylalkyl, heteroaryloxy, heteroarylalkoxy, acyl, hydroxy$C_{1\text{-}6}$-alkyl, $C_{1\text{-}6}$-alkyl-amino, $C_{1\text{-}6}$-dialkylamino, arylamino, arylalkylamino, amino$C_{1\text{-}6}$-alkyl, $C_{1\text{-}6}$-alkoxy$C_{1\text{-}6}$-alkyl, aryloxy$C_{1\text{-}6}$-alkyl, or arylalkoxy$C_{1\text{-}6}$-alkyl.

In another preferred embodiment, the present invention is concerned with compounds of formula I wherein $A^1$ and $A^2$ are independently of each other a 5–6 membered cyclic ring or a 9–10 membered bicyclic ring, optionally substituted with one or more halogen, $C_{1\text{-}6}$-alkyl, $C_{1\text{-}6}$-alkoxy, or aryl.

In another preferred embodiment, the present invention is concerned with compounds of formula I wherein $A^1$ and $A^2$ are independently of each other a 5–6 membered cyclic ring optionally substituted with one or more halogen, $C_{1\text{-}6}$-alkyl, $C_{1\text{-}6}$-alkoxy, or aryl.

In another preferred embodiment, the present invention is concerned with compounds of formula I wherein Z is a carbon atom at the end of a double bond, or Z is $CR^3$, wherein $R^3$ is hydrogen, halogen, perhalomethyl, $C_{1\text{-}12}$-alkyl, $C_{4\text{-}12}$alkenynyl, $C_{2\text{-}12}$-alkenyl, $C_{2\text{-}12}$-alkynyl, $C_{1\text{-}12}$-alkoxy, aryloxy, arylalkoxy, heteroaryloxy, heteroarylalkoxy, acyl, acyloxy, hydroxy$C_{1\text{-}12}$-alkyl, $C_{1\text{-}12}$-alkoxy$C_{1\text{-}12}$-alkyl, aryloxy$C_{1\text{-}12}$-alkyl, arylalkoxy$C_{1\text{-}12}$-alkyl, thio$C_{1\text{-}12}$-alkyl, —$COR^4$, or —$SO_2R^{11}$, wherein $R^4$ and $R^{11}$ independently of each other are selected from hydroxy, halogen, perhalomethyl, $C_{1\text{-}6}$-alkoxy or amino optionally substituted with one or more $C_{1-6}$-alkyl, perhalomethyl or aryl optionally substituted with one or more halogen, perhalomethyl, hydroxy, nitro or cyano.

In another preferred embodiment, the present invention is concerned with compounds of formula I wherein Z is a carbon atom at the end of a double bond, or Z is $CR^3$, wherein $R^3$ is hydrogen, halogen, perhalomethyl, $C_{1-6}$-alkyl, $C_{4-6}$-alkenynyl, $C_{2-6}$-alkenyl, $C_{2-6}$-alkynyl, $C_{1-6}$-alkoxy, aryloxy, arylalkoxy, heteroaryloxy, heteroarylalkoxy, acyl, acyloxy, hydroxy$C_{1-6}$-alkyl, $C_{1-6}$-alkoxy$C_{1-6}$-alkyl, aryloxy$C_{1-6}$-alkyl, arylalkoxy$C_{1-6}$-alkyl, thio$C_{1-6}$-alkyl, —$COR^4$, or —$SO_2R^4$, wherein $R^4$ and $R^{11}$ independently of each other are selected from hydroxy, halogen, perhalomethyl, $C_{1-6}$-alkoxy or amino optionally substituted with one or more $C_{1-5}$-alkyl, perhalomethyl or aryl optionally substituted with one or more halogen, perhalomethyl, hydroxy, nitro or cyano.

In another preferred embodiment, the present invention is concerned with compounds of formula I wherein Z is a carbon atom at the end of a double bond, or Z is $CR^3$, wherein $R^3$ is hydrogen, halogen, perhalomethyl, $C_{1-6}$-alkyl, $C_{4-6}$-alkenynyl, $C_{2-6}$-alkenyl, $C_{2-6}$-alkynyl, $C_{1-6}$-alkoxy, aryloxy, arylalkoxy, heteroaryloxy, heteroarylalkoxy, $C_{1-6}$-alkoxy$C_1$-alkyl, aryloxy$C_{1-6}$-alkyl, or arylalkoxy$C_{1-6}$-alkyl.

In another preferred embodiment, the present invention is concerned with compounds of formula I wherein Z is a carbon atom at the end of a double bond, or Z is $CR^3$, wherein $R^3$ is hydrogen.

In another preferred embodiment, the present invention is concerned with compounds of formula I wherein Q is O, S, or $NR^{12}$, wherein $R^{12}$ is hydrogen, perhalomethyl, $C_{1-6}$-alkyl, $C_{4-6}$-alkenynyl, $C_{2-6}$-alkenyl, $C_{2-6}$-alkynyl, aryl, arylalkyl, heterocyclyl, heteroaryl, heteroarylalkyl, acyl, hydroxy$C_{1-6}$-alkyl, amino$C_{1-6}$-alkyl, $C_{1-6}$-alkoxycarbonyl, aryloxycarbonyl, arylalkoxycarbonyl, $C_{1-6}$-alkoxy$C_{1-6}$-alkyl, aryloxy$C_{1-6}$-alkyl, arylalkoxy$C_{1-6}$-alkyl, thio$C_{1-6}$-alkyl, —$COR^{13}$, or —$SO_2R^{14}$, wherein $R^{13}$ and $R^{14}$ independently of each other are selected from hydroxy, perhalomethyl, $C_{1-6}$-alkoxy or amino optionally substituted with one or more $C_{1-6}$-alkyl, perhalomethyl or aryl optionally substituted with one or more halogen, or perhalomethyl.

In another preferred embodiment, the present invention is concerned with compounds of formula I wherein Q is O, S or $NR^{12}$, wherein $R^{12}$ is hydrogen, perhalomethyl, $C_{1-6}$-alkyl, aryl, arylalkyl, heteroarylalkyl, or acyl.

In another preferred embodiment, the present invention is concerned with compounds of formula I wherein Q is O or S.

In another preferred embodiment, the present invention is concerned with compounds of formula I wherein Q is O.

In another preferred embodiment, the present invention is concerned with compounds of formula I wherein Ar represents arylene or heteroarylene, or a divalent heterocyclic group each of which can optionally be substituted with one or more halogen, $C_{1-6}$-alkyl or $C_{1-6}$-alkoxy.

In another preferred embodiment, the present invention is concerned with compounds of formula I wherein Ar represents arylene, or heteroarylene.

In another preferred embodiment, the present invention is concerned with compounds of formula I wherein Ar represents arylene.

In another preferred embodiment, the present invention is concerned with compounds of formula I wherein $R^5$ represents hydrogen, hydroxy, halogen, $C_{1-6}$-alkoxy, $C_{1-6}$-alkyl, $C_{4-6}$alkenynyl, $C_{2-6}$-alkenyl, $C_{2-6}$-alkynyl or arylalkyl optionally substituted with one or more halogen, or perhalomethyl or $R^5$ forms a bond together with $R^6$.

In another preferred embodiment, the present invention is concerned with compounds of formula I wherein $R^5$ represents hydrogen, halogen, $C_{1-6}$-alkoxy, $C_{1-6}$-alkyl, or perhalomethyl or $R^5$ forms a bond together with $R^6$.

In another preferred embodiment, the present invention is concerned with compounds of formula I wherein $R^5$ represents hydrogen, halogen or $R^5$ forms a bond together with $R^6$.

In another preferred embodiment, the present invention is concerned with compounds of formula I wherein $R^5$ represents hydrogen.

In another preferred embodiment, the present invention is concerned with compounds of formula I wherein $R^6$ represents hydrogen, $C_{1-6}$-alkoxy, $C_{1-6}$-alkyl, $C_{4-6}$-alkenynyl, $C_{2-6}$-alkenyl, $C_{2-6}$-alkynyl, acyl or arylalkyl optionally substituted with one or more halogen or perhalomethyl or $R^6$ forms a bond together with $R^5$.

In another preferred embodiment, the present invention is concerned with compounds of formula I wherein $R^6$ represents hydrogen, halogen, $C_{1-6}$-alkoxy, or $R^6$ forms a bond together with $R^5$.

In another preferred embodiment, the present invention is concerned with compounds of formula I wherein $R^6$ represents hydrogen, $C_{1-6}$-alkoxy, or $R^6$ forms a bond together with $R^5$.

In another preferred embodiment, the present invention is concerned with compounds of formula I wherein $R^6$ represents hydrogen.

In another preferred embodiment, the present invention is concerned with compounds of formula I wherein M represents $OR^7$, where $R^7$ represents hydrogen, $C_{1-6}$-alkyl, $C_{4-6}$alkenynyl, $C_{2-6}$-alkenyl, $C_{2-6}$-alkynyl, aryl, arylalkyl, $C_{1-6}$-alkoxy$C_{1-6}$-alkyl, $C_{1-6}$-alkoxycarbonyl, aryloxycarbonyl, $C_{1-6}$-alkylaminocarbonyl, arylaminocarbonyl, acyl, heterocyclyl, heteroaryl or heteroarylalkyl groups optionally substituted with one or more halogen, perhalomethyl, hydroxy, nitro or cyano.

In another preferred embodiment, the present invention is concerned with compounds of formula I wherein M represents $OR^7$, where $R^7$ represents hydrogen, $C_{1-6}$-alkyl, $C_{4-6}$-alkenynyl, $C_{2-6}$-alkenyl, $C_{2-4}$-alkynyl, aryl, arylalkyl, $C_{1-6}$-alkoxy$C_{1-6}$-alkyl, heterocyclyl, heteroaryl or heteroarylalkyl groups optionally substituted with one or more halogen, or perhalomethyl.

In another preferred embodiment, the present invention is concerned with compounds of formula I wherein M represents $OR^7$, where $R^7$ represents $C_{1-6}$-alkyl, or M represents $COYR^8$.

In another preferred embodiment, the present invention is concerned with compounds of formula I wherein M represents $OR^7$, where $R^7$ represents ethyl, or M represents $COYR^8$.

In another preferred embodiment, the present invention is concerned with compounds of formula I wherein M represents hydrogen, $C_{1-6}$-alkyl, $C_{4-6}$-alkenynyl, $C_{2-6}$-alkenyl, $C_{2-6}$-alkynyl, aryl, arylalkyl, heterocyclyl, heteroaryl or heteroarylalkyl groups optionally substituted with one or more halogen, perhalomethyl, hydroxy, nitro or cyano.

In another preferred embodiment, the present invention is concerned with compounds of formula I wherein $R^8$ represents hydrogen, $C_{1-6}$-alkyl, $C_{4-6}$-alkenynyl, $C_{2-6}$-alkenyl, $C_{2-6}$-alkynyl, aryl, arylalkyl, heterocyclyl, heteroaryl or heteroarylalkyl groups optionally substituted with one or more halogen, or perhalomethyl.

In another preferred embodiment, the present invention is concerned with compounds of formula I wherein $R^8$ represents hydrogen or $C_{1-6}$alkyl.

In another preferred embodiment, the present invention is concerned with compounds of formula I wherein $R^8$ represents hydrogen, methyl or ethyl.

In another preferred embodiment, the present invention is concerned with compounds of formula I wherein Y represents oxygen, sulphur or $NR^{10}$, where $R^{10}$ represents hydrogen, $C_{1-6}$-alkyl, aryl, hydroxy$C_{1-6}$-alkyl or arylalkyl groups or when Y is $NR^{10}$, $R^8$ and $R^{10}$ may form a 5 or 6 membered nitrogen containing ring, optionally substituted with one or more $C_{1-6}$-alkyl.

In another preferred embodiment, the present invention is concerned with compounds of formula I wherein Y represents oxygen, or $NR^{10}$, where $R^{10}$ represents hydrogen, $C_{1-6}$-alkyl, aryl, or arylalkyl groups, or when Y is $NR^{10}$, $R^8$ and $R^{10}$ may form a 5 or 6 membered nitrogen containing ring, optionally substituted with one or more $C_{1-6}$-alkyl.

In another preferred embodiment, the present invention is concerned with compounds of formula I wherein Y represents oxygen.

In another preferred embodiment, the present invention is concerned with compounds of formula I wherein k is an integer ranging from 1 to 2.

In another preferred embodiment, the present invention is concerned with compounds of formula I wherein n and m are 1.

Preferred compounds of the invention are:
2-Ethoxy-3-{4-[3-phenyl-3-(4-methylphenyl)-allyloxy]-phenyl}-propionic acid ethyl ester,
2-Ethoxy-3-{4-[3-phenyl-3-(4-methylphenyl)-allyloxy]-phenyl}-propionic acid,
3-{4-[3-(2-Chloro-phenyl)-3-phenyl-allyloxy]-phenyl}-2-ethoxy-propionic acid ethyl ester,
3-{4-[3-(2-Chloro-phenyl)-3-phenyl-allyloxy]-phenyl}-2-ethoxy-propionic acid,
3-{4-[3,3-Bis-(4-methoxy-phenyl)-allyloxy]-phenyl}-2-ethoxy-propionic acid ethyl ester,
3-{4-[3,3-Bis-(4-methoxy-phenyl)-allyloxy]-phenyl}-2-ethoxy-propionic acid,
3-{4-[3-Phenyl-3-(biphenyl-4-yl)-allyloxy]-phenyl}-2-ethoxy-propionic acid ethyl ester,
3-{4-[3-Phenyl-3-(biphenyl-4-yl)-allyloxy]-phenyl}-2-ethoxy-propionic acid,
2-Ethoxy-3-{4-[3-phenyl-3-(thiophen-2-yl)-allyloxy]-phenyl}-propionic acid ethyl ester,
2-Ethoxy-3-{4-[3-phenyl-3-(thiophen-2-yl)-allyloxy]-phenyl}-propionic acid,
2-Ethoxy-3-{4-[3-phenyl-3-(pyridin-2-yl)-allyloxy]-phenyl}-propionic acid ethyl ester,
2-Ethoxy-3-{4-[3-phenyl-3-(pyridin-2-yl)-allyloxy]-phenyl}-propionic acid,
3-[4-(3,3-Diphenyl-propoxy)-phenyl]-2-ethoxy-propionic acid ethyl ester,
3-[4-(3,3-Diphenyl-propoxy)-phenyl]-2-ethoxy-propionic acid,
2-Ethoxy-3-{4-[3-phenyl-3-(4-methylphenyl)-propoxy]-phenyl}-propionic acid ethyl ester,
2-Ethoxy-3-{4-[3-phenyl-3-(4-methylphenyl)-propoxy]-phenyl}-propionic acid,
3-{4-[3-Phenyl-3-(biphenyl-4-yl)-propoxy]-phenyl}-2-ethoxy-propionic acid ethyl ester,
3-{4-[3-Phenyl-3-(biphenyl-4-yl)-propoxy]-phenyl}-2-ethoxy-propionic acid,
2-{4-[3,3-Bis-(4-methoxy-phenyl)-allyloxy]-benzyl}-malonic acid dimethyl ester,
(E)-(2S)-2-Ethoxy-3-{4-[3-(4-furan-2-yl-phenyl)-3-phenyl-allyloxy]-phenyl}-propionic acid ethyl ester,
(E)-(2S)-2-Ethoxy-3-{4-[3-(4-furan-2-yl-phenyl)-3-phenyl-allyloxy]-phenyl}-propionic acid,
(E)-(2S)-3-[4-(3-Biphenyl-4-yl-3-phenyl-allyloxy)-phenyl]-2-ethoxy-propionic acid ethyl ester,
(E)-(2S)-3-[4-(3-Biphenyl-4-yl-3-phenyl-allyloxy)-phenyl]-2-ethoxy-propionic acid,
(E, Z)-(2S)-3-[4-(3-Biphenyl-4-yl-3-phenyl-allyloxy)-phenyl]-2-ethoxy-propionic acid ethyl ester,
(E, Z)-(2S)-3-[4-(3-Biphenyl-4-yl-3-phenyl-allyloxy)-phenyl]-2-ethoxy-propionic acid,
3-{4-[3,3-Bis-(3-methyl-thiophen-2-yl)-allyloxy]-phenyl}-2-ethoxy-propionic acid ethyl ester,
3-{4-[3,3-Bis-(4-bromo-phenyl)-allyloxy]-phenyl}-2-ethoxy-propionic acid ethyl ester,
3-{4-[3,3-Bis-(4-bromo-phenyl)-allyloxy]-phenyl}-2-ethoxy-propionic acid,
2-Ethoxy-3-[4-(3-phenyl-3-pyridin-4-yl-allyloxy)-phenyl]-propionic acid ethyl ester,
2-Ethoxy-3-[4-(3-phenyl-3-pyridin-4-yl-allyloxy)-phenyl]-propionic acid,
(E, Z)-(2S)-2-Ethoxy-3-{4-[3-(4-methoxyphenyl)-3-thiophen-2-yl-allyloxy]-phenyl}-propionic acid ethyl ester,
(E, Z)-(2S)-2-Ethoxy-3-{4-[3-(4-methoxyphenyl)-3-thiophen-2-yl-allyloxy]-phenyl}-propionic acid
(E, Z)-(2S)-2-Ethoxy-3-[4-(3-phenyl-3-p-tolyl-allyloxy)-phenyl]-propionic acid ethyl ester,
(E, Z)-(2S)-2-Ethoxy-3-[4-(3-phenyl-3-p-tolyl-allyloxy)-phenyl]-propionic acid,
(2S)-3-[4-(3,3-Diphenyl-allyloxy)-phenyl]-2-ethoxy-propionic acid ethyl ester,
(2S)-3-[4-(3,3-Diphenyl-allyloxy)-phenyl]-2-ethoxy-propionic acid,
(Z)-(2S)-2-Ethoxy-3-{4-[3-(4-fluorophenyl)-3-phenyl-allyloxy]-phenyl}-propionic acid ethyl ester,
(Z)-(2S)-2-Ethoxy-3-{4-[3-(4-fluorophenyl)-3-phenyl-allyloxy]-phenyl}-propionic acid,
(E)-(2S)-2-Ethoxy-3-{4-[3-(4-fluorophenyl)-3-phenyl-allyloxy]-phenyl}-propionic acid ethyl ester,
(E)-(2S)-2-Ethoxy-3-{4-[3-(4-fluorophenyl)-3-phenyl-allyloxy]-phenyl}-propionic acid,
(2S)-3-{4-[3,3-Bis-(4-methoxyphenyl)-allyloxy]-phenyl}-2-ethoxy-propionic acid ethyl ester,
(2S)-3-{4-[3,3-Bis-(4-methoxyphenyl)-allyloxy]-phenyl}-2-ethoxy-propionic acid,
(2S)-3-[4-(3,3-Di-p-tolyl-allyloxy)-phenyl]-2-ethoxy-propionic acid ethyl ester,
(2S)-3-[4-(3,3-Di-p-tolyl-allyloxy)-phenyl]-2-ethoxy-propionic acid,
(Z)-(2S)-3-[4-(3-Biphenyl-4-yl-3-phenyl-allyloxy)-phenyl]-2-ethoxy-propionic acid,
(Z)-(2S)-3-{4-[3-(4-Bromophenyl)-3-phenyl-allyloxy]-phenyl}-2-ethoxy-propionic acid ethyl ester,
(Z)-(2S)-3-{4-[3-(4-Bromophenyl)-3-phenyl-allyloxy]-phenyl}-2-ethoxy-propionic acid,
(2S)-3-[4-(3,3-Bis-biphenyl-4-yl-allyloxy)-phenyl]-2-ethoxy-propionic acid ethyl ester,
(2S)-3-[4-(3,3-Bis-biphenyl-4-yl-allyloxy)-phenyl]-2-ethoxy-propionic acid,
(2S)-3-{4-[3,3-Bis-(4-bromophenyl)-allyloxy]-phenyl}-2-ethoxy-propionic acid ethyl ester,
(2S)-3-{4-[3,3-Bis-(4-bromophenyl)-allyloxy]-phenyl}-2-ethoxy-propionic acid,
(Z)-(2S)-2-Ethoxy-3-{4-[3-(4-furan-2-yl-phenyl)-3-phenyl-allyloxy]-phenyl}-propionic acid ethyl ester,
(Z)-(2S)-2-Ethoxy-3-{4-[3-(4-furan-2-yl-phenyl)-3-phenyl-allyloxy]-phenyl}-propionic acid, (E)-(2S)-3-{4-[3-(4-Bromophenyl)-3-phenyl-allyloxy]-phenyl}-2-ethoxy-propionic acid ethyl ester,
(E)-(2S)-3-{4-[3-(4-Bromophenyl)-3-phenyl-allyloxy]-phenyl}-2-ethoxy-propionic acid,
(2S)-3-{4-[3,3-Bis-(4-furan-2-yl-phenyl)-allyloxy]-phenyl}-2-ethoxy-propionic acid ethyl ester,
(2S)-3-{4-[3,3-Bis-(4-furan-2-yl-phenyl)-allyloxy]-phenyl}-2-ethoxy-propionic acid,
(E, Z)-(2S)-3-[4-(3-Biphenyl-4-yl-3-p-tolyl-allyloxy)-phenyl]-2-ethoxy-propionic acid ethyl ester,
(E, Z)-(2S)-3-[4-(3-Biphenyl-4-yl-3-p-tolyl-allyloxy)-phenyl]-2-ethoxy-propionic acid, and
(E, Z)-(2R)-3-[4-(3-Biphenyl-4-yl-3-phenyl-allyloxy)-phenyl]-2-ethoxy-propionic acid ethyl ester;

or a salt thereof with a pharmaceutically acceptable acid or base, or any optical isomer or mixture of optical isomers, including a racemic mixture, or any tautomeric forms.

In the above structural formulas and throughout the present specification, the following terms have the indicated meaning:

The term "$C_{1-n'}$-alkyl" wherein n' can be from 2 through 12, as used herein, represents a branched or straight or cyclic alkyl group having from one to the specified number of carbon atoms. Examples of such groups include, but are not limited to methyl, ethyl, n-propyl, isopropyl, butyl, isobutyl, sec-butyl, tert-butyl, pentyl, hexyl and the like and cyclopropyl, cyclobutyl, cyclopentyl, cyclohexyl, cycloheptyl and cyclooctyl and the like.

The terms "$C_{2-n'}$-alkenyl" wherein n' can be from 3 through 15, as used herein, represents an olefinically unsaturated branched or straight hydrocarbon group having from 2 to the specified number of carbon atoms and at least one double bond. Examples of such groups include, but are not limited to, vinyl, 1-propenyl, 2-propenyl, allyl, iso-proppenyl, 1,3-butadienyl, 1-butenyl, hexenyl, pentenyl and the like.

The terms "$C_{2-n'}$-alkynyl" wherein n' can be from 3 through 15, as used herein, represents an unsaturated branched or straight hydrocarbon group having from 2 to the specified number of carbon atoms and at least one triple bond. Examples of such groups include, but are not limited to, 1-propynyl, 2-propynyl, 1-butynyl, 2-butynyl, 1-pentynyl, 2-pentynyl and the like.

The terms "$C_{4-n'}$-alkenynyl" wherein n' can be from 5 through 15, as used herein, represent an unsaturated branched or straight hydrocarbon group having from 4 to the specified number of carbon atoms and both at least one double bond and at least one triple bond. Examples of such groups include, but are not limited to, 1-penten-4-yne, 3-penten-1-yne, 1,3-hexadiene-5-yne and the like.

The term "$C_{1-12}$-alkoxy" as used herein, alone or in combination is intended to include those $C_{1-12}$-alkyl groups of the designated length in either a linear or branched or cyclic configuration linked through an ether oxygen having its free valence bond from the ether oxygen. Examples of linear alkoxy groups are methoxy, ethoxy, propoxy, butoxy, pentoxy, hexoxy and the like. Examples of branched alkoxy are isopropoxy, sec-butoxy, tert-butoxy, isopentoxy, isohexoxy and the like. Examples of cyclic alkoxy are cyclopropyloxy, cyclobutyloxy, cyclopentyloxy, cyclohexyloxy and the like.

The term "$C_{1-12}$-alkylthio" as used herein, alone or in combination, refers to a straight or branched or cyclic monovalent substituent comprising a $C_{1-12}$-alkyl group linked through a divalent sulfur atom having its free valence bond from the sulfur atom and having 1 to 12 carbon atoms e.g. methylthio, ethylthio, propylthio, butylthio, pentylthio and the like. Examples of cyclic alkylthio are cyclopropylthio, cyclobutylthio, cyclopentylthio, cyclohexylthio and the like.

The term "$C_{1-12}$-alkylamino" as used herein, alone or in combination, refers to a straight or branched or cyclic monovalent substituent comprising a $C_{1-12}$-alkyl group linked through amino having a free valence bond from the nitrogen atom e.g. methylamino, ethylamino, propylamino, butylamino, pentylamino and the like. Examples of cyclic alkylamino are cyclopropylamino, cyclobutylamino, cyclopentylamino, cyclohexylamino and the like.

The term "hydroxy$C_{1-12}$-alkyl" as used herein, alone or in combination, refers to a $C_{1-12}$-alkyl as defined herein whereto is attached a hydroxy group, e.g. hydroxyethyl, 1-hydroxypropyl, 2-hydroxypropyl and the like.

The term "arylamino" as used herein, alone or in combination, refers to an aryl as defined herein linked through amino having a free valence bond from the nitrogen atom, e.g., phenylamino, naphthylamino and the like.

The term "arylalkylamino" as used herein, alone or in combination, refers to an arylalkyl as defined herein linked through amino having a free valence bond from the nitrogen atom, e.g., benzylamino, phenethylamino, 3-phenylpropylamino, 1-naphthylmethylamino, 2-(1-naphthyl)ethylamino and the like.

The term "amino$C_{1-12}$-alkyl" as used herein, alone or in combination, refers to a $C_{1-12}$-alkyl as defined herein whereto is attached an amino group, e.g., aminoethyl, 1-aminopropyl, 2-aminopropyl and the like.

The term "aryloxycarbonyl" as used herein, alone or in combination, refers to an aryloxy as defined herein linked through a carbonyl having a free valence bond from the carbon atom, e.g., phenoxycarbonyl, 1-naphthyloxycarbonyl or 2-naphthyloxycarbonyl and the like.

The term "arylalkoxycarbonyl" as used herein, alone or in combination, refers to an arylalkoxy as defined herein linked through a carbonyl having a free valence bond from the carbon atom, e.g., benzyloxycarbonyl, phenethoxycarbonyl, 3-phenylpropoxycarbonyl, 1-naphthylmethoxycarbonyl, 2-(1-naphthyl)ethoxycarbonyl and the like.

The term "$C_{1-12}$-alkoxy$C_{1-12}$-alkyl" as used herein, alone or in combination, refers to a $C_{1-12}$alkyl as defined herein whereto is attached a $C_{1-12}$-alkoxy as defined herein, e.g., methoxymethyl, ethoxymethyl, methoxyethyl, ethoxyethyl and the like.

The term "aryloxy$C_{1-12}$-alkyl" as used herein, alone or in combination, refers to a $C_{1-12}$-alkyl as defined herein whereto is attached an aryloxy as defined herein, e.g., phenoxymethyl, phenoxydodecyl, 1-naphthyloxyethyl, 2-naphthyloxypropyl and the like.

The term "arylalkoxy$C_{1-12}$-alkyl" as used herein, alone or in combination, refers to a $C_{1-12}$-alkyl as defined herein whereto is attached an arylalkoxy as defined herein, e.g., benzyloxymethyl, phenethoxydodecyl, 3-phenylpropoxyethyl, 1-naphthylmethoxypropyl, 2-(1-naphthyl)ethoxymethyl and the like.

The term "thio$C_{1-12}$-alkyl" as used herein, alone or in combination, refers to a $C_{1-12}$-alkyl as defined herein whereto is attached a group of formula —SR''' wherein R''' is hydrogen, $C_{1-6}$alkyl or aryl, e.g., thiomethyl, methylthiomethyl, phenylthioethyl and the like.

The term "$C_{1-12}$-alkoxycarbonylamino" as used herein, alone or in combination, refers to a $C_{1-12}$-alkoxycarbonyl as defined herein linked through amino having a free valence bond from the nitrogen atom, e.g., methoxycarbonylamino, carbethoxyamino, propoxycarbonylamino, isopropoxycarbonylamino, n-butoxycarbonylamino, tert-butoxycarbonylamino and the like.

The term "aryloxycarbonylamino" as used herein, alone or in combination, refers to an aryloxycarbonyl as defined herein linked through amino having a free valence bond from the nitrogen atom, e.g., phenoxycarbonylamino, 1-naphthyloxycarbonylamino or 2-naphthyloxycarbonylamino and the like.

The term "arylalkoxycarbonylamino" as used herein, alone or in combination, refers to an arylalkoxycarbonyl as defined herein linked through amino having a free valence bond from the nitrogen atom, e.g., benzyloxycarbonylamino, phenethoxycarbonylamino, 3-phenylpropoxycarbonylamino, 1-naphthylmethoxycarbonylamino, 2-(1-naphthyl)ethoxycarbonylamino and the like.

The term "aryl" is intended to include aromatic rings, such as carboxylic aromatic rings selected from the group consisting of phenyl, naphthyl, (1-naphthyl or 2-naphthyl) and the like optionally substituted with halogen, amino, hydroxy, $C_{1-6}$-alkyl or $C_{1-6}$-alkoxy and the like.

The term "arylene" is intended to include divalent aromatic rings, such as carboxylic aromatic rings selected from the group consisting of phenylene, naphthylene and the like optionally substituted with halogen, amino, hydroxy, $C_{1-6}$-alkyl or $C_{1-6}$-alkoxy and the like.

The term "halogen" means fluorine, chlorine, bromine or iodine.

The term "perhalomethyl" means trifluoromethyl, trichloromethyl, tribromomethyl or triiodomethyl.

The term "$C_{1-6}$-dialkylamino" as used herein refers to an amino group wherein the two hydrogen atoms independently are substituted with a straight or branched, saturated hydrocarbon chain having the indicated number of carbon atoms; such as dimethylamino, N-ethyl-N-methylamino, diethylamino, dipropylamino, N-(n-butyl)-N-methylamino, di(n-pentyl)amino and the like.

The term "acyl" as used herein refers to a monovalent substituent comprising a $C_{1-6}$-alkyl group linked through a carbonyl group; such as, e.g., acetyl, propionyl, butyryl, isobutyryl, pivaloyl, valeryl and the like.

The term "acyloxy" as used herein refers to acyl as defined herein linked to an oxygen atom having its free valence bond from the oxygen atom, e.g., acetyloxy, propionyloxy, butyryloxy, isobutyryloxy, pivaloyloxy, valeryloxy and the like.

The term "$C_{1-12}$-alkoxycarbonyl" as used herein refers to a monovalent substituent comprising a $C_{1-12}$-alkoxy group linked through a carbonyl group; such as, e.g., methoxycarbonyl, carbethoxy, propoxycarbonyl, isopropoxycarbonyl, n-butoxycarbonyl, sec-butoxycarbonyl, tert-butoxycarbonyl, 3-methylbutoxycarbonyl, n-hexoxycarbonyl and the like.

The term "heteroaryl" as used herein, alone or in combination, refers to a monovalent substituent comprising a 5–6 membered monocyclic aromatic system or a 9–10 membered bicyclic aromatic system containing one or more heteroatoms selected from nitrogen, oxygen and sulfur, e.g., furan, thiophene, pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine and the like.

The term "heteroarylene" as used herein, alone or in combination, refers to a divalent group comprising a 5–6 membered monocyclic aromatic system or a 9–10 membered bicyclic aromatic system containing one or more heteroatoms selected from nitrogen, oxygen and sulfur, e.g., furan, thiophene, pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine and the like.

The term "heteroaryloxy" as used herein, alone or in combination, refers to a heteroaryl as defined herein linked to an oxygen atom having its free valence bond from the oxygen atom e.g. pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine linked to oxygen, and the like.

The term "arylalkyl" as used herein refers to a straight or branched saturated carbon chain containing from 1 to 6 carbons substituted with an aromatic carbohydride; such as benzyl, phenethyl, 3-phenylpropyl, 1-naphthylmethyl, 2-(1-naphthyl)ethyl and the like.

The term "aryloxy" as used herein refers to phenoxy, 1-naphthyloxy, 2-naphthyloxy and the like.

The term "arylalkoxy" as used herein refers to a $C_{1-6}$-alkoxy group substituted with an aromatic carbohydride, such as benzyloxy, phenethoxy, 3-phenylpropoxy, 1-naphthylmethoxy, 2-(1-naphthyl)ethoxy and the like.

The term "heteroarylalkyl" as used herein refers to a straight or branched saturated carbon chain containing from 1 to 6 carbons substituted with a heteroaryl group, such as (2-furyl)methyl, (3-furyl)methyl, (2-thienyl)methyl, (3-thienyl)methyl, (2-pyridyl)methyl, 1-methyl)-(2-pyrimidyl)ethyl and the like.

The term "heteroarylalkoxy" as used herein refers to a heteroarylalkyl as defined herein linked to an oxygen atom having its free valence bond from the oxygen atom, e.g., (2-furyl)methyl, (3-furyl)methyl, (2-thienyl)methyl, (3-thienyl)methyl, (2-pyridyl)methyl, 1-methyl)-(2-pyrimidyl)ethyl linked to oxygen, and the like.

The term "acylamino" as used herein refers to an amino group wherein one of the hydrogen atoms is substituted with an acyl group, such as, e.g., acetamido, propionamido, isopropylcarbonylamino and the like.

The term "$(C_{1-12}$-cycloalkyl)$C_{1-6}$-alkyl" as used herein, alone or in combination, refers to a straight or branched, saturated hydrocarbon chain having 1 to 6 carbon atoms and being monosubstituted with a $C_{3-6}$-cycloalkyl group, the cycloalkyl group optionally being mono- or polysubstituted with $C_{1-6}$-alkyl, halogen, hydroxy or $C_{1-6}$-alkoxy; such as, e.g., cyclopropylmethyl, (1-methylcyclopropyl)methyl, 1-(cyclopropyl)ethyl, cyclopentylmethyl, cyclohexylmethyl and the like.

The term "arylthio" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy; e.g., phenylthio, (4-methylphenyl)- thio, (2-chlorophenyl)thio and the like.

The term "$C_{1-6}$-alkylaminocarbonyl" as used herein refers to a monovalent substituent comprising a $C_{1-6}$-monoalkylamino group linked through a carbonyl group such as, e.g., methylaminocarbonyl, ethylaminocarbonyl, n-propylaminocarbonyl, isopropylaminocarbonyl, n-butylaminocarbonyl, sec-butylaminocarbonyl, isobutylaminocarbonyl, tert-butylaminocarbonyl, n-pentylaminocarbonyl, 2-methylbutylaminocarbonyl, 3-methylbutylaminocarbonyl, n-hexylaminocarbonyl, 4-methylpentylaminocarbonyl, neopentylaminocarbonyl, n-hexylaminocarbonyl and 2-2-dimethylpropylaminocarbonyl and the like.

As used herein, the phrase "heterocyclyl" means a monovalent saturated or unsaturated non aromatic group being monocyclic and containing one or more, such as from one to four carbon atom(s), and from one to four N, O or S atom(s) or a combination thereof. The phrase "heterocyclyl" includes, but is not limited to, 5-membered heterocycles having one hetero atom (e.g. pyrrolidine, pyrroline and the like); 5-membered heterocycles having two heteroatoms in 1, 2 or 1,3 positions (e.g. pyrazoline, pyrazolidine, 1,2-oxathiolane, imidazolidine, imidazoline, 4-oxazolone and the like); 5-membered heterocycles having three heteroatoms (e.g. tetrahydrofurazan and the like); 5-membered heterocycles having four heteroatoms; 6-membered heterocycles with one heteroatom (e.g., piperidine and the like); 6-membered heterocycles with two heteroatoms (e.g., piperazine, morpholine and the like); 6-membered heterocycles with three heteroatoms; and 6-membered heterocycles with four heteroatoms, and the like.

As used herein, the phrase "a divalent heterocyclic group" means a divalent saturated or unsaturated system being monocyclic and containing one or more, such as from one to four carbon atom(s), and one to four N, O or S atom(s) or a combination thereof. The phrase a divalent heterocyclic group includes, but is not limited to, 5-membered heterocycles having one hetero atom (e.g., pyrrolidine, pyrroline and the like); 5-membered heterocycles having two heteroatoms in 1, 2 or 1,3 positions (e.g. pyrazoline, pyrazolidine, 1,2-oxathiolane, imidazolidine, imidazoline, 4-oxazolone and the like); 5-membered heterocycles having three heteroatoms (e.g. tetrahydrofurazan and the like); 5-membered heterocycles having four heteroatoms; 6-membered heterocycles with one heteroatom (e.g. piperidine and the like); 6-membered heterocycles with two heteroatoms (e.g. piperazine, morpholine and the like); 6-membered heterocycles with three heteroatoms; and 6-membered heterocycles with four heteroatoms, and the like.

As used herein, the phrase "a 5–6 membered cyclic ring" means an unsaturated or saturated or aromatic system containing one or more carbon atoms and optionally from one to four N, O or S atom(s) or a combination thereof. The phrase "a 5–6 membered cyclic ring" includes, but is not limited to, e.g. cyclopentyl, cyclohexyl, phenyl, cyclohexenyl, pyrrolidinyl, pyrrolinyl, imidazolidinyl, pyrazolidinyl, pyrazolinyl, piperidyl, piperazinyl, pyrrolyl, 2H-pyrrolyl, imidazolyl, pyrazolyl, triazolyl, pyridyl, pyrazinyl, pyrimidinyl, pyridazinyl, morpholinyl, thiomorpholinyl, isothiazolyl, isoxazolyl, oxazolyl, oxadiazolyl, thiadiazolyl, 1,3-dioxolanyl, 1,4-dioxolanyl and the like, 5-membered heterocycles having one hetero atom (e.g., thiophenes, pyrroles, furans and the like); 5-membered heterocycles having two heteroatoms in 1, 2 or 1,3 positions (e.g. oxazoles, pyrazoles, imidazoles, thiazoles, purines and the like); 5-membered heterocycles having three heteroatoms (e.g., triazoles, thiadiazoles and the like); 5-membered heterocycles having four heteroatoms; 6-membered heterocycles with one heteroatom (e.g. pyridine, quinoline, isoquinoline, phenanthridine, cyclohepta[b]pyridine and the like); 6-membered heterocycles with two heteroatoms (e.g. pyridazines, cinnolines, phthalazines, pyrazines, pyrimidines, quinazolines, morpholines and the like); 6-membered heterocycles with three heteroatoms (e.g., 1,3,5-triazine and the like); and 6-membered heterocycles with four heteroatoms and the like.

As used herein, the phrase "a 9–10 membered bicyclic ring" means an unsaturated or saturated or aromatic system containing one or more carbon atoms and optionally from one to four N, O or S atom(s) or a combination thereof. The phrase "a 9–10 membered bicyclic ring" includes but is not limited to napthalene, quinoline, isoquinoline, indole, benzothiophene, benzofuran and the like.

Certain of the above defined terms may occur more than once in the above formula (I), and upon such occurrence each term shall be defined independently of the other.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley Interscience, 1981). More specifically the compound of formula I may be converted to a 1:1 mixture of diastereomeric amides by treating with chiral amines, amino acids, amino alcohols derived from amino acids; conventional reaction conditions may be employed to convert acid into an amide; the dia-stereomers may be separated either by fractional crystallization or chromatography and the stereoisomers of compound of formula I may be prepared by hydrolysing the pure diastereomeric amide.

Various polymorphs of compound of general formula I forming part of this invention may be prepared by crystallization of compound of formula I under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, ir spectroscopy, differential scanning calorimetry, powder X-ray diffraction or such other techniques.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

Furthermore, the present compounds of formula I can be utilized in the treatment and/or prevention of conditions mediated by nuclear receptors, in particular the Peroxisome Proliferator-Activated Receptors (PPAR).

In a further aspect, the present invention relates to a method of treating and/or preventing Type I or Type II diabetes.

In a still further aspect, the present invention relates to the use of one or more compounds of formula I or pharmaceutically acceptable salts thereof for the preparation of a medicament for the treatment and/or prevention of Type I or Type II diabetes.

In a still further aspect, the present compounds are useful for the treatment and/or prevention of IGT.

In a still further aspect, the present compounds are useful for the treatment and/or prevention of Type 2 diabetes.

In a still further aspect, the present compounds are useful for the delaying or prevention of the progression from IGT to Type 2 diabetes.

In a still further aspect, the present compounds are useful for the delaying or prevention of the progression from non-insulin requiring Type 2 diabetes to insulin requiring Type 2 diabetes.

In another aspect, the present compounds reduce blood glucose and triglyceride levels and are accordingly useful for the treatment and/or prevention of ailments and disorders such as diabetes or obesity.

In still another aspect, the present compounds are useful for the treatment and/or prophylaxis of insulin resistance (Type 2 diabetes), impaired glucose tolerance, dyslipidemia, disorders related to Syndrome X such as hypertension, obesity, insulin resistance, hyperglycaemia, atherosclerosis, hyperlipidemia, coronary artery disease, myocardial ischemia and other cardiovascular disorders.

In still another aspect, the present compounds are effective in decreasing apoptosis in mammalian cells such as beta cells of Islets of Langerhans.

In still another aspect, the present compounds are useful for the treatment of certain renal diseases including glomerulonephritis, glomerulosclerosis, nephrotic syndrome, hypertensive nephrosclerosis.

In still another aspect, the present compounds may also be useful for improving cognitive functions in dementia, treating diabetic complications, psoriasis, polycystic ovarian syndrome (PCOS) and prevention and treatment of bone loss, e.g. osteoporosis.

The invention also relates to pharmaceutical compositions comprising, as an active ingredient, at least one compound of the formula I or any optical or geometric isomer or tautomeric form thereof including mixtures of these or a pharmaceutically acceptable salt thereof together with one or more pharmaceutically acceptable carriers or diluents.

Furthermore, the invention relates to the use of compounds of formula I or their tautomeric forms, their stereoisomers, their polymorphs, their pharmaceutically acceptable salts or pharmaceutically acceptable solvates thereof for the preparation of a pharmaceutical composition for the treatment and/or prevention of conditions mediated by nuclear receptors, in particular the Peroxisome Proliferator-Activated Receptors (PPAR) such as the conditions mentioned above.

The present invention also relates to a process for the preparation of the above said novel compounds, their derivatives, their analogs, their tautomeric forms, their stereoisomers, their polymorphs, their pharmaceutically acceptable salts or pharmaceutically acceptable solvates.

The method comprises:

a) Reacting a compound of formula (II) where $A^1$ and $A^2$ are as defined previously with a phosphonate ester in a Horner Emmons reaction

to give a compound of formula III where $A^1$ and $A^2$ and n are as defined previously,

whereupon a compound of formula III can be reduced with diisobutyl aluminium hydride to give a compound of formula IV where $A^1$ and $A^2$ and n are as defined previously.

Alternatively a compound of formula IV can be prepared via reaction of a compound of formula II with (Ph₃P)₃PCH₂(CH₂)ₙCH₂OH.Br and BuLi in a Wittig reaction.

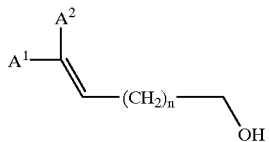
(IV)

The alcohol group in a compound of formula IV can undergo a Mitsunobo reaction with a compound of formula V, alternatively it can be converted to a suitable leaving group (mesyloxy, halide) and react under alkylating conditions with a compound of formula V, wherein Q is OH, SH or amino, Ar, M, Y and R⁵–R⁸ are as defined previously.

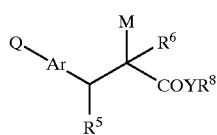
(V)

to give a compound of formula 1, wherein k=1 and A¹, A², Q, Ar, M, Y, n and R⁵–R⁸ are as defined previously.

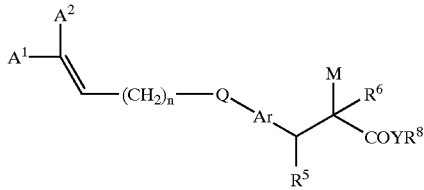
(I)

Ester deprotection of a compound of formula (I) can be carried out using standard hydrolysis techniques, to give a compound of formula 1, wherein Y is O, k=1 and A¹, A², Q, Ar, M, n and R⁵–R⁸ are as defined previously.

Hydrogenating a compound of formula IV under palladium catalysis to give a compound of formula VI wherein A¹ and A² and n are as defined previously:

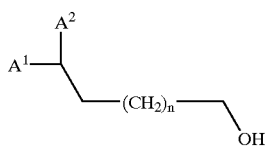
(VI)

A compound of formula VI can undergo a Mitsunobo reaction with a compound of formula V to give a compound of formula 1, wherein k=2 and A¹, A², Q, Ar, M, Y, n and R⁵–R⁸ are as defined previously.

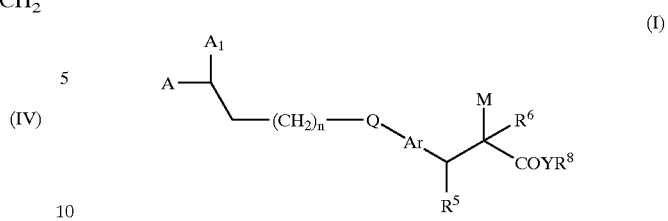
(I)

Ester deprotection of a compound of formula (I) can be carried out using standard hydrolysis techniques, to give a compound of formula 1, wherein Y is O, k=2 and A¹, A², Q, Ar, M, n and R⁵–R⁸ are as defined previously.

Pharmacological Methods

In Vitro PPAR Alpha and PPAR Gamma Activation Activity.

Principle

The PPAR gene transcription activation assays were based on transient transfection into human HEK293 cells of two plasmids encoding a chimeric test protein and a reporter protein respectively. The chimeric test protein was a fusion of the DNA binding domain (DBD) from the yeast GAL4 transcription factor to the ligand binding domain (LBD) of the human PPAR proteins. The PPAR LBD harbored in addition to the ligand binding pocket also the native activation domain (activating function 2=AF2) allowing the fusion protein to function as a PPAR ligand dependent transcription factor. The GAL4 DBD will force the fusion protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing in the absence of ligand. Upon addition to the cells of a PPAR ligand, luciferase protein will be produced in amounts corresponding to the activation of the PPAR protein. The amount of luciferase protein is measured by light emission after addition of the appropriate substrate.

Methods

Cell culture and transfection: HEK293 cells were grown in DMEM+10% FCS, 1% PS. Cells were seeded in 96-well plates the day before transfection to give a confluency of 80% at transfection. 0.8 µg DNA per well was transfected using FuGene transfection reagent according to the manufacturers instructions (Boehringer-Mannheim). Cells were allowed to express protein for 48 h followed by addition of compound.

Plasmids: Human PPAR α and γ was obtained by PCR amplification using cDNA templates from liver, intestine and adipose tissue respectively. Amplified cDNAs were cloned into pCR2.1 and sequenced. The LBD from each isoform PPAR was generated by PCR (PPARα: aa 167—C-term; PPARγ: aa 165—C-term) and fused to GAL4-DBD by subcloning fragments in frame into the vector pM1 generating the plasmids pM1αLBD and pM1γLBD. Ensuing fusions were verified by sequencing. The reporter was constructed by inserting an oligonucleotide encoding five repeats of the Gal4 recognition sequence into the pGL2 vector (Promega).

Compounds: All compounds were dissolved in DMSO and diluted 1:1000 upon addition to the cells. Cells were treated with compound (1:1000 in 200 μl growth medium including delipidated serum) for 24 h followed by luciferase assay.

Luciferase assay: Medium including test compound was aspirated and 100 μl PBS incl. 1 mM Mg++ and Ca++ was added to each well. The luciferase assay was performed using the LucLite kit according to the manufacturers instructions (Packard Instruments). Light emission was quantified by counting SPC mode on a Packard Instruments top-counter.

Pharmaceutical Compositions

In another aspect, the present invention includes within its scope pharmaceutical compositions comprising, as an active ingredient, an effective amount of at least one of the compounds of formula I or a pharmaceutically acceptable salt thereof together with a pharmaceutically acceptable carrier or diluent.

The present compounds may also be administered in combination with one or more further pharmacologically active substances, e.g., selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Suitable antidiabetics comprise insulin, GLP-1 (glucagon like peptide-1) derivatives such as those disclosed in WO 98/08871 to Novo Nordisk A/S, which is incorporated herein by reference as well as orally active hypoglycemic agents.

The orally active hypoglycemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as HMG CoA inhibitors (statins), compounds lowering food intake, RXR agonists and agents acting on the ATP-dependent potassium channel of the β-cells.

In one embodiment of the invention the present compounds are administered in combination with insulin.

In a further embodiment the present compounds are administered in combination with a sulphonylurea, e.g., tolbutamide, glibenclamide, glipizide or glicazide.

In another embodiment the present compounds are administered in combination with a biguanide, e.g., metformin.

In yet another embodiment the present compounds are administered in combination with a meglitinid, e.e.g., repaglinide.

In a further embodiment the present compounds are administered in combination with an α-glucosidase inhibitor, e.g., miglitol or acarbose.

In another embodiment the present compounds are administered in combination with an agent acting on the ATP-dependent potassium channel of the β-cells, e.g., tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent, e.g., cholestyramine, colestipol, clofibrate, gemfibrozil, lovastatin, pravastatin, simvastatin, probucol or dextrothyroxine.

In a further embodiment the present compounds are administered in combination with more than one of the above-mentioned compounds, e.g., in combination with a sulphonylurea and metformin, a sulphonylurea and acarbose, repaglinide and metformin, insulin and a sulphonylurea, insulin and metformin, insulin, insulin and lovastatin, etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

Pharmaceutical compositions containing a compound of the present invention may be prepared by conventional techniques, e.g., as described in Remington: The Science and Practise of Pharmacy, 19$^{th}$ Ed., 1995. The compositions may appear in conventional forms, for example capsules, tablets, aerosols, solutions, suspensions or topical applications.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 5 mg |
| Colloidal silicon dioxide (AEROSIL) | 1.5 mg |
| Cellulose, microcryst. (AVICEL) | 70 mg |
| Modified cellulose gum (AC-DI-SOL) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

The compounds of the invention may be administered to a mammal, especially a human in need of such treatment, prevention, elimination, alleviation or amelioration of diseases related to the regulation of blood sugar. Such mammals include also animals, both domestic animals, e.g., household pets, and non-domestic animals such as wildlife.

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen for patients it may frequently be necessary to begin with a dosage of from about 2 to about 70 mg per day and when the condition is under control to reduce the dosage as low as from about 0.1 to about 10 mg per day. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 0.1 to about 100 mg of active ingredient together with a pharmaceutically acceptable carrier per unit dosage.

Usually, dosage forms suitable for oral, nasal, pulmonary or transdermal administration comprise from about 0.001 mg to about 100 mg, preferably from about 0.01 mg to about 50 mg of the compounds of formula I admixed with a pharmaceutically acceptable carrier or diluent.

Any novel feature or combination of features described herein is considered essential to this invention.

EXAMPLES

The process for preparing compounds of formula 1, and preparations containing them, is further illustrated in the following examples, which however, are not to be construed as limiting.

The structures of the compounds are confirmed by either elemental analysis (MA) nuclear magnetic resonance (NMR) or mass spectrometry (MS). NMR shifts (d) are given in parts per million (ppm) and only selected peaks are given. mp is melting point and is given in °C. Column chromatography was carried out using the technique described by W. C. Still et al, J. Org. Chem. 1978, 43, 2923–2925 on Merck silica gel 60 (Art 9385). Compounds used as starting materials are either known compounds or compounds which can readily be prepared by methods known per se.

Abbrevations:
TLC: thin layer chromatography
DMSO: dimethylsulfoxide
CDCl$_3$: deutorated chloroform
DMF: N,N-dimethylformamide
min: minutes
h: hours

Example 1

(E,Z)-2-Ethoxy-3-{4-[3-phenyl-3-(4-methylphenyl)-allyloxy]-phenyl}-propionic acid ethyl ester To a solution of 3-phenyl-3-(4-methyl-phenyl)-prop-2-en-1-ol (150 mg, 0.6 mmol), triphenylphosphine (195 mg, 0.73 mmol) and 2-ethoxy-3-(4-hydroxy-phenyl)-propionic acid ethyl ester (190 mg, 0.79 mmol) in THF at ice bath temperature was added diethylazodicarboxylate (0.11 ml, 0.73 mmol) and the reaction stirred 1.5 h at this temperature and 16 h at room temperature. Ice water was added and the crude product isolated by a dichloromethane extraction and brine wash. Concentration under reduced pressure and flash chromatography gave the title compound (300 mg).

$^1$H NMR (CDCl$_3$, 300 MHz); δ 1.07-1.28 (6H, 2×CH$_3$), 2.30 and 2.40 (3H, CH$_3$), 2.90–2.93 (2H, CH$_2$), 3.30–3.40 and 3.51–3.61 (2H, OCH$_2$), 3.90–4.0 (1H, CHCO$_2$), 4.10–4.19 (2H, OCH$_2$), 4.41–4.61 (2H, OCH$_2$) 6.23–6.32 (1H, CHalkene), 6.70–6.81 (2H, aryl), 7.03–7.45 (remaining H, aryl).

MS calcd for C$_{29}$H$_{32}$O$_4$ 444.6, Found 444.2

Example 2

(E,Z)-2-Ethoxy-3-{4-[3-phenyl-3-(4-methylphenyl)-allyloxy]-phenyl}-propionic acid (E,Z)-2-Ethoxy-3{-4-[3-phenyl-3-(4-methylphenyl)-allyloxy]-phenyl}-propionic acid ethyl ester (example 1) (80 mg, 0.18 mmol) was hydrolyzed in 1N NaOH (0.35 mL) and ethanol (0.35 mL) for 4 h at room temperature and 16 h at 5° C. Water (1 mL) was added and the reaction mixture was neutralised with 6N HCl. The crude product was extracted with dichloromethane and concentrated under reduced pressure. Flash chromatography gave the title compound (48 mg).

$^1$H NMR (CDCl$_3$, 300 MHz); δ 1.07–1.20 (3H, CH$_3$), 2.32 and 2.40 (3H, CH$_3$), 2.85–3.10 (2H, CH$_2$), 3.30–3.45 and 3.51–3.68 (2H, OCH$_2$), 3.95–4.06 (1H, CHCO$_2$), 4.51.4.61 (2H, OCH$_2$) 6.21–6.41 (1H, CHalkene), 6.72–6.82 (2H, aryl), 7.03–7.50 (remaining H, aryl).

MS calcd for C$_{27}$H$_{28}$O$_4$ 416.5, Found 416.3.

Example 3

(E, Z)-3-{4-[3-(2-Chloro-phenyl)-3-phenyl-allyloxy]-phenyl}-2-ethoxy-propionic acid ethyl ester To a solution of 3-(2-chloro-phenyl)-3-phenyl-prop-2-en-1-ol (370 mg, 1.5 mmol), tributyl-phosphine (0.5 mL, 1.6 mmol) and 2-ethoxy-3-(4-hydroxy-phenyl)-propionic acid ethyl ester (380 mg, 1.6 mmol) in benzene at ice bath temperature was added azodicarboxylic dipiperidide (403 mg, 1.6 mmol) and the reaction stirred 1 h. Work up and purification as for Example 1 gave the title compound (490 mg).

$^1$H NMR (CDCl$_3$, 300 MHz); δ 1.07–1.30 (6H, 2×CH$_3$), 2.90–2.95 (2H, CH$_2$), 3.29–3.40 and 3.52–3.63 (2H, OCH$_2$), 3.90–4.0 (1H, CHCO$_2$), 4.10–4.20 (2H, OCH$_2$), 4.35–4.56 and 4.70–4.80 (2H, OCH$_2$), 6.00–6.08 and 6.42–6.53 (1H, CHalkene), 6.70–6.81 (2H, aryl), 7.06–7.55 (remaining H, aryl).

MS calcd for C$_{28}$H$_{29}$ClO$_4$ 465.0, Found 464.2.

Example 4

(E, Z)-3-{4-[3-(2-Chloro-phenyl)-3-phenyl-allyloxy]-phenyl}-2-ethoxy-propionic acid (E, Z)-3-{4-[3-(2-Chloro-phenyl)-3-phenyl-allyloxy]-phenyl}-2-ethoxy-propionic acid ethyl ester (example 3) (400 mg, 0.86 mmol) was hydrolyzed in an identical manner to example 2 to give the title compound (353 mg).

$^1$H NMR (CDCl$_3$, 300 MHz); δ 1.09–1.20 (3H, CH$_3$), 2.85–3.10 (2H, CH$_2$), 3.30–3.42 and 3.51–3.65 (2H, OCH$_2$), 3.96–4.05 (1H, CHCO$_2$), 4.35–4.50 and 4.70–4.74 (2H, OCH$_2$) 6.00–6.05 and 6.42–6.49 (1H, CHalkene), 6.71–6.82 (2H, aryl), 7.05–7.50 (remaining H, aryl).

MS calcd for C$_{26}$H$_{25}$ClO$_4$ 436.9, Found 436.2.

Example 5

3-{4-[3,3-Bis-(4-methoxy-phenyl)-allyloxy]-phenyl}-2-ethoxy-propionic acid ethyl ester Reaction of 3,3-bis(4-methoxy-phenyl)-prop-2-en-1-ol (216 mg, 0.8 mmol), triphenylphosphine (240 mg, 0.9 mmol), 2-ethoxy-3-(4-hydroxy-phenyl)-propionic acid ethyl ester (240 mg, 1.0 mmol) and diethylazodicarboxylate (0.11 mL, 0.9 mmol) in an identical manner to Example 1 gave the title compound (90 mg).

$^1$H NMR (CDCl$_3$, 300 MHz); δ 1.10-1.30 (6H, 2×CH$_3$), 2.90–2.95 (2H, CH$_2$), 3.29–3.39 and 3.52–3.65 (2H, OCH$_2$), 3.78 (3H, OCH$_3$), 3.82 (3H, OCH$_3$), 3.90–3.99 (1H, CHCO$_2$), 4.10–4.20 (2H, OCH2), 4.51–4.59 (1H, OCH$_2$) 6.12–6.19 (1H, CHalkene), 6.70–7.45 (remaining H, aryl).

MS calcd for C$_{30}$H$_{34}$O$_6$ 490.6, Found 488.3.

Example 6

3-{4-[3,3-Bis-(4-methoxy-phenyl)-allyloxy]-phenyl}-2-ethoxy-propionic acid

3-{4-[3,3-Bis-(4-methoxy-phenyl)-allyloxy]-phenyl}-2-ethoxy-propionic acid ethyl ester (example 5) (80 mg, 0.16 mmol) was hydrolyzed in an identical manner to example 2 to give the title compound (29 mg).

$^1$H NMR (CDCl$_3$, 300 MHz); δ 1.12–1.20 (3H, CH$_3$), 2.87–3.09 (2H, CH$_2$), 3.32–3.49 and 3.52–3.63 (2H, OCH$_2$), 3.78 (3H, OCH$_3$), 3.82 (3H, OCH$_3$), 3.99–4.02 (1H, CHCO$_2$), 4.51–4.55 (1H, OCH$_2$) 6.12-6.19 (1H, CHalkene), 6.72-7.23 (remaining H, aryl).

MS calcd for C$_{28}$H$_{30}$O$_6$ 462.5, Found 462.1.

Example 7

(E, Z)-3-{4-[3-phenyl-3-(Biphenyl-4-yl)-allyloxy]-phenyl}-2-ethoxy-propionic acid ethyl ester Reaction of of 3-phenyl-3-(biphenyl-4-yl)-prop-2-en-1-ol (250 mg, 0.66 mmol), triphenylphosphine (195 mg, 0.73 mmol), 2-ethoxy-3-(4-hydroxy-phenyl)-propionic acid ethyl ester (190 mg, 0.79 mmol) and diethylazodicarboxylate (0.11 mL, 0.79 mmol) in an identical manner to Example 1 gave the title compound (180 mg).

$^1$H NMR (CDCl$_3$, 300 MHz); δ 1.10–1.32 (6H, 2×CH$_3$), 2.89–2.95 (2H, CH$_2$), 3.28–3.39 and 3.52–3.63 (2H, OCH$_2$), 3.91–3.96 (1H, CHCO$_2$), 4.08–4.20 (2H, OCH$_2$), 4.51–4.62 (1H, OCH$_2$) 6.29–6.41 and 6.61–6.70 (1H, CHalkene), 6.72–7.80 (2H, aryl), 7.08–7.18 (2H, aryl), 7.20–7.70 (remaining H, aryl).

MS calcd for C$_{34}$H$_{34}$O$_4$ 506.6, Found 504.2.

Example 8

(E, Z)-3-{4-[3-phenyl-3-(Biphenyl-4-yl)-allyloxy]-phenyl}-2-ethoxy-propionic acid (E, Z)-3-{4-[3-phenyl-3-(Biphenyl-4-yl)-allyloxy]-phenyl}-2-ethoxy-propionic acid ethyl ester (example 7) (70 mg, 0.13 mmol) was hydrolyzed in an identical manner to example 2 to give the title compound (25 mg).

$^1$H NMR (CDCl$_3$, 300 MHz); δ 1.02–1.23 (3H, CH$_3$), 2.83–3.12 (2H, CH$_2$), 3.32–3.50 and 3.52–3.63 (2H, OCH$_2$), 3.96–4.07 (1H, CHCO$_2$), 4.51–4.70 (1H, OCH$_2$) 6.39–6.41 (1H, CHalkene), 6.72–7.82 (2H, aryl), 7.01–7.65 (remaining H, aryl).

MS calcd for C$_{32}$H$_{30}$O$_4$ 478.6, Found 478.2

Example 9

(E, Z)-2-Ethoxy-3-{4-[3-phenyl-3-(thiophen-2-yl)-allyloxy]-phenyl}-propionic acid ethyl ester Reaction of 3-phenyl-3-(thiophen-2-yl)-prop-2-en-1-ol (320 mg, 1.5 mmol), tributylphosphine (0.4 mL, 1.6 mmol), 2-ethoxy-3-(4-hydroxy-phenyl)-propionic acid ethyl ester (380 mg, 1.6 mmol) and azodicarboxylic dipiperidide (403 mg, 1.6 mmol) in an identical manner to Example 3 gave the title compound (290 mg).

$^1$H NMR (CDCl$_3$, 300 MHz); δ 1.08–1.32 (6H, 2×CH$_3$), 2.90–2.99 (2H, CH$_2$), 3.28–3.39 and 3.52–3.63 (2H, OCH$_2$), 3.91–3.99 (1H, CHCO$_2$), 4.08–4.21 (2H, OCH$_2$), 4.42–4.50 and 4.72–4.80 (1H, OCH$_2$), 6.19–6.25 and 6.32–6.39 (1H, CHalkene), 6.62–7.48 (remaining H, aryl).

MS calcd for C$_{26}$H$_{28}$O$_4$S 436.6, Found 436.1.

Example 10

(E, Z)-2-Ethoxy-3-{4-[3-phenyl-3-(thiophen-2-yl)-allyloxy]-phenyl}-propionic acid (E, Z)-2-Ethoxy-3-{4-[3-phenyl-3-(thiophen-2-yl)-allyloxy]-phenyl}-propionic acid ethyl ester (example 9) (200 mg, 0.45 mmol) was hydrolyzed in an identical manner to example 2 to give the title compound (94 mg).

$^1$H NMR (CDCl$_3$, 300 MHz); δ 1.12–1.31 (3H, CH$_3$), 2.88–3.10 (2H, CH$_2$), 3.28–3.48 and 3.52–3.58 (2H, OCH$_2$), 3.96–4.03 (1H, CHCO$_2$), 4.42–4.48 and 4.76–4.80 (1H, OCH$_2$), 6.19–6.22 and 6.32–6.39 (1H, CHalkene), 6.65–7.48 (remaining H, aryl).

MS calcd for C$_{24}$H$_{24}$O$_4$S 408.5, Found 408.2.

Example 11

2-Ethoxy-3-{4-[3-phenyl-3-(Pyridin-2-yl)-allyloxy]-phenyl}-propionic acid ethyl ester Reaction of 3-phenyl-3-(pyridin-2-yl)-prop-2-en-1-ol (320 mg, 1.5 mmol), tributylphosphine (0.42 mL, 1.6 mmol), 2-ethoxy-3-(4-hydroxy-phenyl)-propionic acid ethyl ester (380 mg, 1.6 mmol) and azodicarboxylic dipiperidide (403 mg, 1.6 mmol) in an identical manner to Example 3 gave the title compound (650 mg).

$^1$H NMR (CDCl$_3$, 300 MHz); δ 1.10–1.30 (6H, 2×CH$_3$), 2.90–2.95 (2H, CH$_2$), 3.28–3.39 and 3.51-3.62 (2H, OCH$_2$), 3.90-3.95 (1H, CHCO$_2$), 4.05–4.20 (2H, OCH$_2$), 4.53–4.59 (1H, OCH$_2$) 6.72–6.78 (1H, CHalkene), 6.95–7.60 (remaining H, aryl and pyridyl), 8.58–8.61 (1H, pyridyl).

MS calcd for C$_{27}$H$_{29}$O$_4$N 431.5, Found 431.3.

Example 12

2-Ethoxy-3-{4-[3-phenyl-3-(pyridin-2-yl)-allyloxy]-phenyl}-propionic acid

2-Ethoxy-3-{4-[3-phenyl-3-(pyridin-2-yl)-allyloxy]-phenyl}-propionic acid ethyl ester (example 11) (210 mg, 0.48 mmol) was hydrolyzed in an identical manner to example 2 to give the title compound (110 mg).

$^1$H NMR (CDCl$_3$, 300 MHz); δ1.10–1.18 (3H, CH$_3$), 2.82–3.04 (2H, CH$_2$), 3.28–3.39 and 3.51–3.62 (2H, OCH$_2$), 3.92–3.97 (1H, CHCO$_2$), 4.53–4.65 (1H, OCH$_2$) 6.70–6.78 (1H, CHalkene), 6.88–7.62 (remaining H, aryl and pyridyl), 8.58–8.62 (1H, pyridyl).

MS calcd for C$_{25}$H$_{25}$O$_4$N 403.5, Found 403.2.

Example 13

3-[4-(3,3-Diphenyl-propoxy)-phenyl]-2-ethoxy-propionic acid ethyl ester

Reaction of 3,3-diphenyl-propan-1-ol (110 mg, 0.5 mmol), triphenylphosphine (145 mg, 0.55 mmol), 2-ethoxy-3-(4-hydroxy-phenyl)-propionic acid ethyl ester (140 mg, 0.6 mmol) and diethylazodicarboxylate (0.09 mL, 0.55 mmol) in an identical manner to Example 1 gave the title compound (120 mg).

$^1$H NMR (CDCl$_3$, 300 MHz); δ 1.10–1.29 (6H, 2×CH$_3$), 2.44–2.55 (2H, CH$_2$), 2.90–2.95 (2H, CH$_2$), 3.28–3.39 and 3.51–3.62 (2H, OCH$_2$), 3.80–3.89 (2H, CH$_2$), 3.90–3.95 (1H, CHCO$_2$), 4.10–4.28 (3H, arylCH and OCH$_2$), 6.70–6.77 (2H, aryl), 7.05–7.35 (remaining H, aryl).

MS calcd for C$_{28}$H$_{32}$O$_4$ 432.6, Found 432.3.

Example 14

3-[4-(3,3-Diphenyl-propoxy)-phenyl]-2-ethoxy-propionic acid

3-[4-(3,3-Diphenyl-propoxy)-phenyl]-2-ethoxy-propionic acid ethyl ester (example 13) (110 mg, 0.25 mmol) was hydrolyzed in an identical manner to example 2 to give the title compound (55 mg).

$^1$H NMR (CDCl$_3$, 300 MHz); δ 1.10–1.19 (3H, CH$_3$), 2.42–2.55 (2H, CH$_2$), 2.87–3.08 (2H, CH$_2$), 3.30–3.47 and 3.51–3.62 (2H, OCH$_2$), 3.80–3.89 (2H, CH$_2$), 3.98–4.03

(1H, CHCO$_2$), 4.10–4.25 (1H, arylCH), 6.70–6.77 (2H, aryl), 7.05–7.35 (remaining H, aryl).

MS calcd for C$_{26}$H$_{28}$O$_4$ 404.5, Found 404.3.

Example 15

2-Ethoxy-3-{4-[3-phenyl-3-(4-methylphenyl)-propoxy]-phenyl}-propionic acid ethyl ester

Reaction of 3-phenyl-3-(4-methylphenyl)-2-propann-1-ol (210 mg, 0.88 mmol), tributylphosphine (0.25 mL, 1.0 mmol), 2-ethoxy-3-(4-hydroxy-phenyl)-propionic acid ethyl ester (240 mg, 1.0 mmol) and azodicarboxylic dipiperidide (250 mg, 1.0 mmol) in an identical manner to Example 3 gave the title compound (160 mg).

$^1$H NMR (CDCl$_3$, 300 MHz); δ 1.07–1.28 (6H, 2×CH$_3$), 2.29 (3H, CH$_3$), 2.42–2.49 (2H, CH$_2$), 2.89–2.93 (2H, CH$_2$), 3.25–3.40 and 3.51–3.61 (2H, OCH$_2$), 3.88–3.85 (2H, CH$_2$), 3.90–4.00 (1H, CHCO$_2$), 4.10–4.19 (3H, arylCH and OCH$_2$), 6.69–6.73 (2H, aryl), 7.03–7.29 (remaining H, aryl).

MS calcd for C$_{29}$H$_{34}$O$_4$ 446.6, Found 446.3.

Example 16

2-Ethoxy-3-{4-[3-phenyl-3-(4-methylphenyl)-propoxy]-phenyl}-propionic acid

2-Ethoxy-3-{4-[3-phenyl-3-(4-methylphenyl)-propoxy]-phenyl}-propionic acid ethyl ester (example 15) (130 mg, 0.30 mmol) was hydrolyzed in an identical manner to example 2 to give the title compound (55 mg).

$^1$H NMR (CDCl$_3$, 300 MHz); δ 1.11–1.21 (3H, CH$_3$), 2.29 (3H, CH$_3$), 2.42–2.53 (2H, CH$_2$), 2.83–3.12 (2H, CH$_2$), 3.38–3.50 and 3.51–3.63 (2H, OCH$_2$), 3.80–3.88 (2H, CH$_2$), 3.99–4.05 (1H, CHCO$_2$), 4.12–4.22 (1H, arylCH), 6.69–6.73 (2H, aryl), 7.03–7.29 (remaining H, aryl).

MS calcd for C$_{27}$H$_{30}$O$_4$ 418.5, Found 418.3.

Example 17

3-{4-[3-phenyl-3-(biphenyl-4-yl)-propoxy]-phenyl}-2-ethoxy-propionic acid ethyl ester

Reaction of 3-biphenyl-4-yl-3-phenyl-propan-1-ol (145 mg, 0.5 mmol), triphenylphosphine (145 mg, 0.55 mmol), 2-ethoxy-3-(4-hydroxy-phenyl)-propionic acid ethyl ester (140 mg, 0.6 mmol) and diethylazodicarboxylate (0.09 mL, 0.55 mmol) in an identical manner to Example 1 gave the title compound (230 mg).

$^1$H NMR (CDCl$_3$, 300 MHz); δ 1.07–1.28 (6H, 2×CH$_3$), 2.48–2.55 (2H, CH$_2$), 2.89–2.93 (2H, CH$_2$), 3.25–3.40 and 3.51–3.63 (2H, OCH$_2$), 3.88–4.00 (3H, CH$_2$ and CHCO$_2$), 4.10–4.19 (2H, OCH$_2$), 4.20–4.30 (1H, CH), 6.67–6.71 (2H, aryl), 7.05–7.55 (remaining H, aryl).

MS calcd for C$_{34}$H$_{36}$O$_4$ 508.7, Found 508.3.

Example 18

3-{4-[3-phenyl-3-(biphenyl-4-yl)-propoxy]-phenyl}-2-ethoxy-propionic acid

3-{4-[3-phenyl-3-(biphenyl-4-yl)-propoxy]-phenyl}-2-ethoxy-propionic acid ethyl ester (example 17) (200 mg, 0.39 mmol) was hydrolyzed in an identical manner to example 2 to give the title compound (70 mg).

$^1$H NMR (CDCl$_3$, 300 MHz); δ 1.07–1.20 (3H, CH$_3$), 2.49–2.61 (2H, CH$_2$), 2.88–3.09 (2H, CH$_2$), 3.32–3.48 and 3.51–3.66 (2H, OCH$_2$), 3.88–3.92 (2H, CH$_2$) 3.95–4.05 (1H, CHCO$_2$), 4.20–4.30 (1H, CH), 6.67–6.79 (2H, aryl), 7.05–7.55 (remaining H, aryl).

MS calcd for C$_{32}$H$_{32}$O$_4$ 480.6, Found 480.3.

Example 19

2-{4-[3,3-Bis-(4-methoxy-phenyl)-allyloxy]-benzyl}-malonic acid dimethyl ester

Under a nitrogen atmosphere, 3,3-bis-(4-methoxy-phenyl)-prop-2-en-1-ol (500 mg, 1.95 mmol), tributylphosphine (424 (mg, 2.1 mmol) and 2-(4-hydroxy-benzyl)-malonic acid dimethyl ester (464 mg, 1.95 mmol) were successively dissolved in dry benzene (50 mL). Solid azodicarboxylic dipiperidide (ADDP) (530 mg, 2.1 mmol) was added under stirring at 0° C. to the solution. After 10 min, the reaction mixture was brought to room temperature and the stirring was continued for 16 h. Heptane (10 mL) was added to the reaction mixture and di hydro-ADDP separated out was filtered off. After evaporation of the solvent the product was purified by chromatography eluting with heptane/ethylacetate (4:1) to give 150 mg (16%) of the title compound.

$^1$H NMR (CDCl$_3$, 300 MHz); δ 3.15 (2H, PhCH$_2$), 3.63 (1H, CH), 3.70 (6H, 2×CO$_2$CH$_3$), 3.80 (3H, PhOCH$_3$), 3.83 (3H, PhOCH$_3$), 4.55 (1H, OCH$_2$), 6.15 (1H, CHalkene), 6.70–7.20 (remaining H, aryl).

Example 20

(E)-(2S)-2-Ethoxy-3-{4-[3-(4-furan-2-yl-phenyl)-3-phenyl-allyloxy]-phenyl}-propionic acid ethyl ester

Reaction of (E)-3-(4-furan-2-yl-phenyl)-3-phenyl-prop-2-en-1-ol (475 mg, 1.72 mmol), tributylphosphine (0.63 ml, 2.58 mmol), (2S)-2-ethoxy-3-(4-hydroxy-phenyl)-propionic acid ethyl ester (451 mg, 1.89 mmol) and azodicarboxylic dipiperidide (650 mg, 2.58 mmol) in benzene in an identical manner to example 3 gave the title compound (450 mg, 53%).

$^1$H NMR (CDCl$_3$, 300 MHz); δ 1.16 (3H, t), 1.21 (3H, t), 2.93 (2H, d), 3.26–3.40 (1H, m), 3.52–3.64 (1H, m), 3.94 (1H, t), 4.14 (2H, q), 4.58 (2H, d), 6.36 (1H, t), 6.47 (1H, dd), 6.63 (1H, d), 6.77 (2H, dm), 7.12 (2H, dm), 7.16–7.31 (4H, m), 7.31–7.50 (4H, m), 7.58 (2H, dm).

Example 21

(E)-(2S)-2-Ethoxy-3-{4-[3-(4-furan-2-yl-phenyl)-3-phenyl-allyloxy]-phenyl}-propionic acid

(E)-(2S)-2-Ethoxy-3-{4-[3-(4-furan-2-yl-phenyl)-3-phenyl-allyloxy]-phenyl}-propionic acid ethyl ester (example 20) (440 mg, 0.89 mmol) was hydrolyzed in an identical manner to example 2 to give the title compound (408 mg, 97%).

$^1$H NMR (CDCl$_3$, 300 MHz); δ 1.17 (3H, t), 2.93 (1H, dd), 3.07 (1H, dd), 3.39–3.52 (1H, m), 3.52–3.64 (1H, m), 4.04 (1H, dd), 4.58 (2H, d), 6.36 (1H, t), 6.48 (1H, m), 6.63 (1H, d), 6.79 (2H, dm), 7.12 (2H, dm), 7.16–7.32 (4H, m), 7.32–7.50 (4H, m), 7.59 (2H, dm), COOH too broad to be observed.

LCMS (electrospray): 491 (M+Na), 259 (100%).

Example 22

(E)-(2S)-3-[4-(3-Biphenyl-4-yl-3-phenyl-allyloxy)-phenyl]-2-ethoxy-propionic acid ethyl ester Reaction of (E)-3-biphenyl-4-yl-3-phenyl-prop-2-en-1-ol (1.0 g, 3.49 mmol), tributylphosphine (1.3 ml, 5.24 mmol), (2S)-2-ethoxy-3-(4-hydroxy-phenyl)-propionic acid ethyl ester (0.92 g, 3.84 mmol) and azodicarboxylic dipiperidide (1.32 g, 5.24 mmol) in benzene in an identical manner to example 3 gave the title compound (1.47 g, 83%).

$^1$H NMR (CDCl$_3$, 300 MHz); δ 1.16 (3H, t), 1.21 (3H, t), 2.95 (2H, d), 3.28–3.40 (1H, m), 3.53–3.65 (1H, m), 3.95 (1H, t), 4.15 (2H, q), 4.57 (2H, d), 6.39 (1H, t), 6.78 (2H, dm), 7.12 (2H, dm), 7.20–7.48 (10H, m), 7.48–7.62 (4H, m).

Example 23

(E)-(2S)-3-[4-(3-Biphenyl-4-yl-3-phenyl-allyloxy)-phenyl]-2-ethoxy-propionic acid (E)-(2S)-3-[4-(3-Biphenyl-4-yl-3-phenyl-allyloxy)-phenyl]-2-ethoxy-propionic acid ethyl ester (example 22) (1.38 g, 2.72 mmol) was hydrolyzed in an identical manner to example 2 to give the title compound (1.25 mg, 96%).

$^1$H NMR (CDCl$_3$, 300 MHz); δ 1.17 (3H, t), 2.95 (1H, dd), 3.06 (1H, dd), 3.37–3.52 (1H, m), 3.52–3.64 (1H, m), 4.03 (1H, dd), 4.59 (2H, d), 6.38 (1H, t), 6.78 (2H, m), 7.12 (2H, dm), 7.20–7.49 (10H, m), 7.49–7.62 (4H, m), COOH too broad to be observed.

Example 24

(E, Z)-(2S)-3-[4-(3-Biphenyl-4-yl-3-phenyl-allyloxy)-phenyl]-2-ethoxy-propionic acid ethyl ester Reaction of (E, Z)-3-biphenyl-4-yl-3-phenyl-prop-2-en-1-ol (601 mg, 2.1 mmol), triphenylphosphine (606 mg, 2.31 mmol), (2S)-2-ethoxy-3-(4-hydroxy-phenyl)-propionic acid ethyl ester (601 mg, 2.52 mmol) and diethy lazodicarboxylate (402 mg, 2.31 mmol) in an identical manner to example 1 gave the title compound (400 mg, 38%).

$^1$H NMR (CDCl$_3$, 200 MHz); δ 1.10–1.30 (6H, m), 2.94 (2H, d), 3.25-3.45 (1H, m), 3.50–3.65 (1H, m), 3.96 (1H, t), 4.16 (2H, dd), 4.55–4.68 (2H, d), 6.30–6.44 (1H, m), 6.73–6.84 (2H, m), 7.14 (2H, dm), 7.20–7.70 (14H, m).

Example 25

(E, Z)-(2S)-3-[4-(3-Biphenyl-4-yl-3-phenyl-allyloxy)-phenyl]-2-ethoxy-propionic acid (E, Z)-(2S)-3-[4-(3-Biphenyl-4-yl-3-phenyl-allyloxy)-phenyl]-2-ethoxy-propionic acid ethyl ester (example 24) (400 mg, 0.79 mmol) was hydrolyzed in an identical manner to example 2 to give the title compound (250 mg, 66%).

$^1$H NMR (CDCl$_3$, 300 MHz); δ 1.05–1.20 (3H, m), 2.94 (1H, dd), 3.01 (1H, dd), 3.30–3.43 (1H, m), 3.50–3.68 (1H, m), 4.00 (1H, dd), 4.50–4.68 (2H, m), 6.27–6.40 (1H, m), 6.72–6.84 (2H, m), 7.12 (2H, dm), 7.18–7.65 (14H, m), 9.85 (1H, br s).

Example 26

3-{4-[3,3-Bis-(3-methyl-thiophen-2-yl)-allyloxy]-phenyl}-2-ethoxy-propionic acid ethyl ester Reaction of 3,3-bis-(3-methylthiophen-2-yl)-prop-2-en-1-ol (1.0 mg, 3.99 mmol), tributylphosphine (0.91 g, 4.5 mmol), 2-ethoxy-3-(4-hydroxy-phenyl)-propionic acid ethyl ester (1.07 g, 4.5 mmol) and azodicarboxylic dipiperidide (1.14 g, 4.5 mmol) in an identical manner to example 3 gave the title compound (680 mg, 36%).

$^1$H NMR (CDCl$_3$, 200 MHz); δ 1.15 (3H, t), 1.23 (3H, t), 2.00 (3H, s), 2.08 (3H, s), 2.93 (2H, d), 3.28–3.40 (1H, m), 3.50–3.64 (1H, m), 3.94 (1H, t), 4.14 (2H, dd), 4.58 (2H, d), 6.24 (1H, t), 6.70–6.81 (3H, m), 6.88 (1H, d), 7.04–7.15 (3H, m), 7.21–7.30 (1H, m).

Example 27

3-{4-[3,3-Bis-(4-bromo-phenyl)-allyloxy]-phenyl}-2-ethoxy-propionic acid ethyl ester Reaction of 3,3-bis-(4-bromophenyl)-prop-2-en-1-ol (0.50 g, 1.36 mmol), triphenylphosphine (0.39 g, 1.50 mmol), 2-ethoxy-3-(4-hydroxy-phenyl)-propionic acid ethyl ester (0.39 g, 1.63 mmol) and diethy lazodicarboxylate (0.26 g, 1.51 mmol) in an identical manner to example 1 gave the title compound (450 mg, 56%).

$^1$H NMR (CDCl$_3$, 300 MHz); δ 1.15 (3H, t), 1.22 (3H, t), 2.94 (2H, d), 3.28–3.42 (1H, m), 3.53–3.65 (1H, m), 3.96 (1H, t), 4.16 (2H, q), 4.52 (2H, d), 6.32 (1H, t), 6.75 (2H, dm), 7.01–7.20 (6H, m), 7.43 (2H, dm), 7.52 (2H, dm).

MS (EI): 586/588/590 (M$^+$), 513/515/517, 349/351/353 (100%).

Example 28

3-{4-[3,3-Bis-(4-bromo-phenyl)-allyloxy]-phenyl}-2-ethoxy-propionic acid

3-{4-[3,3-Bis-(4-bromo-phenyl)-allyloxy]-phenyl}-2-ethoxy-propionic acid ethyl ester (example 27) (150 mg, 0.25 mmol) was hydrolyzed in an identical manner to example 2 to give the title compound (135 mg, 96%).

$^1$H NMR (CDCl$_3$, 300 MHz); δ 1.17 (3H, t), 2.94 (1H, dd), 3.06 (1H, dd), 3.40–3.52 (1H, m), 3.52–3.66 (1H, m), 4.04 (1H, dd), 4.51 (2H, d), 6.30 (1H, t), 6.76 (2H, dm), 7.00–7.20 (6H, m), 7.42 (2H, dm), 7.52 (2H, dm), COOH too broad to be observed.

MS (EI): 558/560/562 (M$^+$), 349/351/353, 270/272 (100%), 191.

Example 29

2-Ethoxy-3-[4-(3-phenyl-3-pyridin-4-yl-allyloxy)-phenyl]-propionic acid ethyl ester Reaction of 3-phenyl-3-pyridin-4-yl-prop-2-en-1-ol (0.50 g, 2.37 mmol), triphenylphosphine (0.68 g, 2.61 mmol), 2-ethoxy-3-(4-hydroxy-phenyl)-propionic acid ethyl ester (0.68 g, 2.84 mmol) and diethyl azodicarboxylate (0.46 g, 2.63 mmol) in an identical manner to example 1 gave the title compound (435 mg, 43%).

$^1$H NMR (CDCl$_3$, 200 MHz); δ 1.16 (3H, t), 1.21 (3H, t), 2.94 (2H, d), 3.25–3.43 (1H, m), 3.50–3.70 (1H, m), 3.98 (1H, t), 4.17 (2H, q), 4.52 (2H, d), 6.41 (1H, t), 6.76 (2H, dm), 7.05–7.40 (9H, m), 8.66 (2H, dm).

MS (EI): 431 (M+), 194 (100%).
Mp. 84–87° C.

Example 30

2-Ethoxy-3-[4-(3-phenyl-3-pyridin-4-yl-allyloxy)-phenyl]-propionic acid

2-Ethoxy-3-[4-(3-phenyl-3-pyridin-4-yl-allyloxy)-phenyl]-propionic acid ethyl ester (example 29) (200 mg, 0.46 mmol) was hydrolyzed in an identical manner to example 2 to give the title compound (50 mg, 27%).

$^1$H NMR (CDCl$_3$, 300 MHz); δ 1.16 (3H, t), 2.98 (1H, dd), 3.06 (1H, dd), 3.33–3.49 (1H, m), 3.60–3.75 (1H, m), 4.03 (1H, dd), 4.52 (2H, d), 6.46 (1H, t), 6.78 (2H, dm), 7.09–7.40 (9H, m), 8.63 (2H, dm), 9.23 (1H, br s).

Example 31

(E, Z)-(2S)-2-Ethoxy-3-{4-[3-(4-methoxyphenyl)-3-thiophen-2-yl-allyloxy]-phenyl}-propionic acid ethyl ester Reaction of 3-(4-methoxyphenyl)-3-thiophen-2-yl-prop-2-en-1-ol (271 mg, 1.10 mmol), triphenylphosphine (289 mg, 1.10 mmol), (2S)-2-ethoxy-3-(4-hydroxy-phenyl)-propionic acid ethyl ester (238 mg, 1.0 mmol) and diethyl azodicarboxylate (188 mg, 1.08 mmol) in an identical manner to example 1 gave the title compound (80 mg, 17%).

$^1$H NMR (CDCl$_3$, 200 MHz); δ 1.10–1.28 (6H, m), 2.88–2.98 (2H, m), 3.25–3.43 (1H, m), 3.47–3.69 (1H, m), 3.77–3.90 (3H, m), 3.95 (1H, tm), 4.16 (2H, q), 4.45–4.78 (2H, m), 6.10–6.48 (1H, m), 6.70–7.50 (11H, m).

Example 32

(E, Z)-(2S)-2-Ethoxy-3-{4-[3-(4-methoxyphenyl)-3-thiophen-2-yl-allyloxy]-phenyl}-propionic acid (E, Z)-(2S)-2-Ethoxy-3-{4-[3-(4-methoxyphenyl)-3-thiophen-2-yl-allyloxy]-phenyl}-propionic acid ethyl ester (example 31) (75 mg, 0.16 mmol) was hydrolyzed in an identical manner to example 2 to give the title compound (40 mg, 57%).

$^1$H NMR (CDCl$_3$, 300 MHz); δ 1.17 (3H, t), 2.83–3.13 (2H, m), 3.27–3.50 (1H, m), 3.50–3.70 (1H, m), 3.77–3.88 (3H, m), 3.97–4.09 (1H, m), 4.43–4.28 (2H, m), 6.10–6.30 (1H, m), 6.70–7.40 (11H, m), COOH too broad to be observed.

MS (EI): 438 (M+), 229 (100%).

Example 33

(E, Z)-(2S)-2-Ethoxy-3-[4-(3-phenyl-3-p-tolyl-allyloxy)-phenyl]-propionic acid ethyl ester Reaction of (E, Z)-3-phenyl-3-tolyl-prop-2-en-1-ol (841 mg, 3.75 mmol), triphenylphosphine (1.03 g, 3.93 mmol), (2S)-2-ethoxy-3-(4-hydroxy-phenyl)-propionic acid ethyl ester (851 mg, 3.57 mmol) and diethy lazodicarboxylate (656 mg, 3.94 mmol) in an identical manner to example 1 gave the title compound (0.64 g, 40%).

$^1$H NMR (CDCl$_3$, 300 MHz); δ 1.14 (3H, t), 1.22 (3H, t), 2.30–2.42 (3H, m), 2.93 (2H, d), 3.26–3.40 (1H, m), 3.51–3.66 (1H, m), 3.94 (1H, t), 4.16 (2H, q), 4.49–4.63 (2H, m), 6.20–6.33 (1H, m), 6.76 (2H, dm), 7.00–7.45 (11H, m).

MS (EI): 444 (M+), 207 (100%).

Example 34

(E, Z)-(2S)-2-Ethoxy-3-[4-(3-phenyl-3-p-tolyl-allyloxy)-phenyl]-propionic acid (E, Z)-(2S)-2-Ethoxy-3-[4-(3-phenyl-3-p-tolyl-allyloxy)-phenyl]-propionic acid ethyl ester (example 33) (0.55 g, 1.24 mmol) was hydrolyzed in an identical manner to example 2 to give the title compound (0.50 g, 97%).

$^1$H NMR (CDCl$_3$, 300 MHz); δ 1.17 (3H, t), 2.24–2.41 (3H, m), 2.93 (1H, dd), 3.04 (1H, dd), 3.37–3.64 (2H, m), 4.03 (1H, dd), 4.50–4.63 (2H, m), 6.20–6.32 (1H, m), 6.78 (2H, dm), 7.00–7.43 (11H, m), COOH too broad to be observed.

MS (EI): 416 (M+), 207 (100%).

Example 35

(2S)-3-[4-(3,3-Diphenyl-allyloxy)-phenyl]-2-ethoxy-propionic acid ethyl ester

Reaction of 3,3-diphenyl-prop-2-en-1-ol (210 mg, 1.0 mmol), tributylphosphine (303 mg, 1.50 mmol), (2S)-2-ethoxy-3-(4-hydroxy-phenyl)-propionic acid ethyl ester (250 mg, 1.05 mmol) and azodicarboxylic dipiperidide (378 mg, 1.50 mmol) in an identical manner to example 3 gave the title compound (290 mg, 67%).

$^1$H NMR (CDCl$_3$, 300 MHz); δ 1.14 (3H, t), 1.21 (3H, t), 2.92 (2H, d), 3.28–3.40 (1H, m), 3.52–3.65 (1H, m), 3.94 (1H, t), 4.14 (2H, q), 4.56 (2H, d), 6.31 (1H, t), 6.75 (2H, dm), 7.10 (2H, dm), 7.16–7.44 (10H, m).

Example 36

(2S)-3-[4-(3,3-Diphenyl-allyloxy)-phenyl]-2-ethoxy-propionic acid (2S)-3-[4-(3,3-Diphenyl-allyloxy)-phenyl]-2-ethoxy-propionic acid ethyl ester (example 35) (215 mg, 0.50 mmol) was hydrolyzed in an identical manner to example 2 to give the title compound (180 mg, 90%).

$^1$H NMR (CDCl$_3$, 300 MHz); δ 1.17 (3H, t), 2.93 (1H, dd), 3.04 (1H, dd), 3.38–3.50 (1H, m), 3.50–3-63 (1H, m), 4.03 (1H, dd), 4.58 (2H, d), 6.31 (1H, t), 6.77 (2H, dm), 7.11 (2H, dm), 7.17–7.43 (10H, m), COOH too broad to be observed.

Example 37

(Z)-(2S)-2-Ethoxy-3-{4-[3-(4-fluorophenyl)-3-phenyl-allyloxy]-phenyl}-propionic acid ethyl ester Reaction of (Z)-3-(4-fluorophenyl)-3-phenyl-prop-2-en-1-ol (200 mg, 0.88 mmol), triphenylphosphine (242 mg, 0.92 mmol), (2S)-2-ethoxy-3-(4-hydroxy-phenyl)-propionic acid ethyl ester (200 mg, 0.84 mmol) and diethyl azodicarboxylate (160 mg, 0.92 mmol) in an identical manner to example 1 gave the title compound (275 mg, 73%).

$^1$H NMR (CDCl$_3$, 300 MHz); δ 1.15 (3H, t), 1.21 (3H, t), 2.93 (2H, d), 3.27–3.40 (1H, m), 3.51–3.65 (1H, m), 3.96 (1H, t), 4.14 (2H, q), 4.54 (2H, d), 6.33 (1H, t), 6.76 (2H, dm), 6.95–7.40 (11H, m).

MS (EI): 448 (M+), 375, 211 (100%).

Example 38

(Z)-(2S)-2-Ethoxy-3-{4-[3-(4-fluorophenyl)-3-phenyl-allyloxy]-phenyl}-propionic acid (Z)-(2S)-2-Ethoxy-3-{4-[3-(4-fluorophenyl)-3-phenyl-allyloxy]-phenyl}-propionic acid ethyl ester (example 37) (200 mg, 0.45 mmol) was hydrolyzed in an identical manner to example 2 to give the title compound (158 mg, 86%).

$^1$H NMR (CDCl$_3$, 200 MHz); δ 1.15 (3H, t), 2.84–3.14 (2H, m), 3.35–3.68 (2H, m), 4.04 (1H, dd), 4.54 (2H, d), 6.32 (1H, t), 6.77 (2H, dm), 7.00–7.40 (11H, m), COOH too broad to be observed.

MS (EI): 420 (M$^+$), 368, 317, 211 (100%).

Example 39

(E)-(2S)-2-Ethoxy-3-{4-[3-(4-fluorophenyl)-3-phenyl-allyloxy]-phenyl}-propionic acid ethyl ester Reaction of (E)-3-(4-fluorophenyl)-3-phenyl-prop-2-en-1-ol (200 mg, 0.88 mmol), triphenylphosphine (242 mg, 0.92 mmol), (2S)-2-ethoxy-3-(4-hydroxy-phenyl)-propionic acid ethyl ester (200 mg, 0.84 mmol) and diethyl azodicarboxylate (160 mg, 0.92 mmol) in an identical manner to example 1 gave the title compound (320 mg, 85%).

$^1$H NMR (CDCl$_3$, 300 MHz); δ 1.15 (3H, t), 1.21 (3H, t), 2.93 (2H, d), 3.24–3.43 (1H, m), 3.50–3.67 (1H, m), 3.96 (1H, t), 4.16 (2H, q), 4.54 (2H, d), 6.25 (1H, t), 6.75 (2H, dm), 6.90–7.03 (2H, m), 7.03–7.30 (6H, m), 7.30–7.45 (3H, m).

MS (EI): 448 (M$^+$), 375, 211 (100%).

Example 40

(E)-(2S)-2-Ethoxy-3-{4-[3-(4-fluorophenyl)-3-phenyl-allyloxy]-phenyl}-propionic acid (E)-(2S)-2-Ethoxy-3-{4-[3-(4-fluorophenyl)-3-phenyl-allyloxy]-phenyl}-propionic acid ethyl ester (example 39) (225 mg, 0.50 mmol) was hydrolyzed in an identical manner to example 2 to give the title compound (245 mg, 95%).

$^1$H NMR (CDCl$_3$, 200 MHz); δ 1.17 (3H, t), 2.83–3.14 (2H, m), 3.34–3.68 (2H, m), 4.02 (1H, dd), 4.53 (2H, d), 6.24 (1H, t), 6.78 (2H, dm), 6.89–7.05 (2H, m), 7.05–7.49 (9H, m), COOH too broad to be observed.

MS (EI): 420 (M$^+$), 317, 211 (100%).

Example 41

(2S)-3-{4-[3,3-Bis-(4-methoxyphenyl)-allyloxy]-phenyl}-2-ethoxy-propionic acid ethyl ester Reaction of 3,3-bis-(4-methoxyphenyl)-prop-2-en-1-ol (1.62 g, 5.99 mmol), triphenylphosphine (2.88 g, 10.98 mmol), (2S)-2-ethoxy-3-(4-hydroxy-phenyl)-propionic acid ethyl ester (1.19 g, 4.99 mmol) and diethy lazodicarboxylate (1.92 g, 11.04 mmol) in an identical manner to example 1 gave the title compound (0.434 g, 17%).

$^1$H NMR (CDCl$_3$, 300 MHz); δ 1.15 (3H, t), 1.21 (3H, t), 2.93 (2H, d), 3.27–3.41 (1H, m), 3.53–3.65 (1H, m), 3.80 (3H, s), 3.84 (3H, s), 3.95 (1H, t), 4.15 (2H, q), 4.56 (2H, d), 6.17 (1H, t), 6.71–6.87 (4H, m), 6.92 (2H, dm), 7.05–7.25 (6H, m).

Example 42

(2S)-3-{4-[3,3-Bis-(4-methoxyphenyl)-allyloxy]-phenyl}-2-ethoxy-propionic acid (2S)-3-{4-[3,3-Bis-(4-methoxyphenyl)-allyloxy]-phenyl}-2-ethoxy-propionic acid ethyl ester (example 41) (225 mg, 0.495 mmol) was hydrolyzed in an identical manner to example 2 to give the title compound (150 mg, 71%).

$^1$H NMR (CDCl$_3$, 300 MHz); δ1.17 (3H, t), 2.95 (1H, dd), 3.04 (1H, dd), 3.38–3.50 (1H, m), 3.52–3.66 (1H, m), 3.80 (3H, s), 3.83 (3H, s), 4.03 (1H, dd), 4.57 (2H, d), 6.17 (1H, t), 6.71–6.85 (4H, m), 6.92 (2H, dm), 7.05–7.25 (6H, m), COOH too broad to be observed.

Example 43

(2S)-3-[4-(3,3-Di-p-tolyl-allyloxy)-phenyl]-2-ethoxy-propionic acid ethyl ester

Reaction of 3,3-di-(4-methylphenyl)-prop-2-en-1-ol (1.0 g, 4.20 mmol), tributylphosphine (1.27 g, 6.30 mmol), (2S)-2-ethoxy-3-(4-hydroxy-phenyl)-propionic acid ethyl ester (1.10 g, 4.62 mmol) and azodicarboxylic dipiperidide (1.59 g, 6.30 mmol) in an identical manner to example 3 gave the title compound (0.76 g, 39%).

$^1$H NMR (CDCl$_3$, 300 MHz); δ 1.13 (3H, t), 1.21 (3H, t), 2.33 (3H, s), 2.38 (3H, s), 2.93 (2H, d), 3.26–3.41 (1H, m), 3.52–3.66 (1H, m), 3.95 (1H, t), 4.15 (2H, q), 4.56 (2H, d), 6.27 (1H, t), 6.75 (2H, dm), 7.00–7.21 (10H, m).

MS (EI): 458 (M$^+$), 385, 221 (100%).

Example 44

(2S)-3-[4-(3,3-Di-p-tolyl-allyloxy)-phenyl]-2-ethoxy-propionic acid (2S)-3-[4-(3,3-Di-p-tolyl-allyloxy)-phenyl]-2-ethoxy-propionic acid ethyl ester (example 43) (0.76 g, 1.66 mmol) was hydrolyzed in an identical manner to example 2 to give the title compound (0.696 g, 98%).

$^1$H NMR (CDCl$_3$, 300 MHz); δ 1.16 (3H, t), 2.33 (3H, s), 2.38 (3H, s), 2.94 (1H, dd), 3.05 (1H, dd), 3.39–3.51 (1H, m), 3.51–3.65 (1H, m), 4.03 (1H, dd), 4.57 (2H, d), 6.23 (1H, t), 6.77 (2H, dm), 7.00–7.22 (10H, m), COOH too broad to be observed.

MS (EI): 430 (M$^+$), 327, 221 (100%).

Example 45

(Z)-(2S)-3-[4-(3-Biphenyl-4-yl-3-phenyl-allyloxy)-phenyl]-2-ethoxy-propionic acid ethyl ester Reaction of (Z)-3-biphenyl-4-yl-3-phenyl-prop-2-en-1-ol (171 mg, 0.60 mmol), triphenylphosphine (142 mg, 0.63 mmol), (2S)-2-ethoxy-3-(4-hydroxy-phenyl)-propionic acid ethyl ester (149 mg, 0.63 mmol) and diethyl azodicarboxylate (95 mg, 0.55 mmol) in an identical manner to example 1 gave the title compound (160 mg, 53%).

$^1$H NMR (CDCl$_3$, 300 MHz); δ 1.16 (3H, t), 1.21 (3H, t), 2.93 (2H, d), 3.28–3.40 (1H, m), 3.52–3.65 (1H, m), 3.95 (1H, t), 4.14 (2H, q), 4.63 (2H, d), 6.33 (1H, t), 6.78 (2H, dm), 7.12 (2H, dm), 7.20–7.50 (10H, m), 7.55–7.68 (4H, m).

Example 46

(Z)-(2S)-3-[4-(3-Biphenyl-4-yl-3-phenyl-allyloxy)-phenyl]-2-ethoxy-propionic acid (Z)-(2S)-3-[4-(3-Biphenyl-4-yl-3-phenyl-allyloxy)-phenyl]-2-ethoxy-propionic acid ethyl ester (example 45) (0.36 g, 0.71 mmol) was hydrolyzed in an identical manner to example 2 to give the title compound (0.345 g, 86%) as an orange gum containing approximately 0.6 molar equivalents of ethyl acetate.

$^1$H NMR (CDCl$_3$, 300 MHz); δ 1.17 (3H, t), 1.26 (1.8H, t, ethyl acetate), 2.04 (1.8H, s, ethyl acetate), 2.95 (1H, dd), 3.06 (1H, dd), 3.38–3.52 (1H, m), 3.52–3.64 (1H, m), 4.03 (1H, dd), 4.12 (1.2H, q, ethyl acetate), 4.63 (2H, d), 6:32 (1H, t), 6.80 (2H, dm), 7.11 (2H, dm), 7.20–7.50 (10H, m), 7.54–7.68 (4H, m), COOH too broad to be observed.

MS (EI): 478 (M$^+$), 375, 269 (100%).

Example 47

(Z)-(2S)-3-{4-[3-(4-Bromophenyl)-3-phenyl-allyloxy]-phenyl}-2-ethoxy-propionic acid ethyl ester Reaction of 3-(4-bromophenyl)-3-phenyl-prop-2-en-1-ol (145 mg, 0.50 mmol), triphenylphosphine (144 mg, 0.55 mmol), (2S)-2-ethoxy-3-(4-hydroxy-phenyl)-propionic acid ethyl ester (119 mg, 0.50 mmol) and diethyl azodicarboxylate (96 mg, 0.55 mmol) in an identical manner to example 1 gave the title compound (110 mg, 43%).

$^1$H NMR (CDCl$_3$, 300 MHz); δ 1.17 (3H, t), 1.21 (3H, t), 2.94 (2H, d), 3.29–3.41 (1H, m), 3.53–3.65 (1H, m), 3.96 (1H, t), 4.15 (2H, q), 4.53 (2H, d), 6.32 (1H, t), 6.75 (2H, dm), 7.05–7.18 (4H, m), 7.18–7.38 (5H, m), 7.52 (2H, dm).

MS (EI): 508/510 (M$^+$) 435/437, 393/395, 271/273, 192 (100%).

Microanalysis for C$_{28}$H$_{29}$BrO$_4$+0.1H$_2$O: calculated=65.78% C, 5.76% H; found 65.79% C, 5.91% H.

Example 48

(Z)-(2S)-3-{4-[3-(4-Bromophenyl)-3-phenyl-allyloxy]-phenyl}-2-ethoxy-propionic acid (Z)-(2S)-3-{4-[3-(4-Bromophenyl)-3-phenyl-allyloxy]-phenyl}-2-ethoxy-propionic acid ethyl ester (example 47) (90 mg, 0.18 mmol) was hydrolyzed in an identical manner to example 2 to give the title compound (60 mg, 71%).

$^1$H NMR (CDCl$_3$, 300 MHz); δ 1.17 (3H, t), 2.96 (1H, dd), 3.05 (1H, dd), 3.39–3.51 (1H, m), 3.51–3.64 (1H, m), 4.03 (1H, dd), 4.52 (2H, d), 6.32 (1H, t), 6.75 (2H, dm), 7.02–7.18 (4H, m), 7.18–7.40 (5H, m), 7.51 (2H, dm), COOH too broad to be observed.

LCMS (electrospray): 503/505 (M+Na), 498/500 (M+NH$_4$), 271/273 (100%).

Example 49

(2S)-3-[4-(3,3-Bis-biphenyl-4-yl-allyloxy)-phenyl]-2-ethoxy-propionic acid ethyl ester Reaction of 3,3-bis-biphenyl-4-yl-prop-2-en-1-ol (363 mg, 1.0 mmol), tributylphosphine (303 mg, 1.5 mmol), (2S)-2-ethoxy-3-(4-hydroxy-phenyl)-propionic acid ethyl ester (262 mg, 1.1 mmol) and azodicarboxylic dipiperidide (378 mg, 1.5 mmol) in an identical manner to example 3 gave the title compound (445 mg, 76%) containing 0.8 equivalents of ethyl acetate.

$^1$H NMR (CDCl$_3$, 300 MHz); δ 1.16 (3H, t), 1.21 (3H, t), 1.25 (2.4H, t, ethyl acetate), 2.04 (2.4H, s, ethyl acetate), 2.93 (2H, d), 3.28–3.40 (1H, m), 3.51–3.65 (1H, m), 3.96 (1H, t), 4.07–4.20 ({2H, q} plus {1.6H, q, ethyl acetate}), 4.54 (2H, d), 6.40 (1H, t), 6.80 (2H, dm), 7.03 (2H, dm), 7.27–7.70 (18H, m).

Example 50

(2S)-3-[4-(3,3-Bis-biphenyl-4-yl-allyloxy)-phenyl]-2-ethoxy-propionic acid (2S)-3-[4-(3,3-Bis-biphenyl-4-yl-allyloxy)-phenyl]-2-ethoxy-propionic acid ethyl ester (example 49) (560 mg, 0.96 mmol) was hydrolyzed in an identical manner to example 2 to give the title compound (450 mg, 84%).

$^1$H NMR (CDCl$_3$, 300 MHz); δ 1.13 (3H, t), 2.93 (1H, dd), 3.05 (1H, dd), 3.35–3.50 (1H, m), 3.50–3.64 (1H, m), 4.02 (1H, dd), 4.62 (2H, d), 6.39 (1H, t), 6.80 (2H, dm), 7.02 (2H, dm), 7.27–7.72 (18H, m), COOH too broad to be observed.

Example 51

(2S)-3-{4-[3,3-Bis-(4-bromophenyl)-allyloxy]-phenyl}-2-ethoxy-propionic acid ethyl ester Reaction of 3,3-bis-(4-bromophenyl)-prop-2-en-1-ol (2.60 g, 7.0 mmol), tributylphosphine (2.52 g, 10.0 mmol), (2S)-2-ethoxy-3-(4-hydroxy-phenyl)-propionic acid ethyl ester (1.50 g, 6.3 mmol) and azodicarboxylic dipiperidide (2.02 g, 10.0 mmol) in an identical manner to example 3 gave the title compound (2.8 g, 75%).

$^1$H NMR (CDCl$_3$, 300 MHz); δ 1.16 (3H, t), 1.21 (3H, t), 2.93 (2H, d), 3.27–3.40 (1H, m), 3.53–3.65 (1H, m), 3.94 (1H, t), 4.15 (2H, q), 4.51 (2H, d), 6.31 (1H, t), 6.75 (2H, dm), 7.01–7.19 (6H, m), 7.42 (2H, dm), 7.52 (2H, dm).

Example 52

(2S)-3-{4-[3,3-Bis-(4-bromophenyl)-allyloxy]-phenyl}-2-ethoxy-propionic acid (2S)-3-{4-[3,3-Bis-(4-bromophenyl)-allyloxy]-phenyl}-2-ethoxy-propionic acid ethyl ester (example 51) (2.8 g, 4.76 mmol) was hydrolyzed in an identical manner to example 2 to give the title compound (2.3 g, 83%) which contained approximately 0.25 molar equivalents of ethyl acetate.

$^1$H NMR (CDCl$_3$, 300 MHz); δ 1.15 (3H, t), 1.25 (0.75H, t, ethyl acetate), 2.04 (0.75H, s, ethyl acetate), 2.93 (1H, dd), 3.04 (1H, dd), 3.37–3.49 (1H, m), 3.52–3.68 (1H, m), 4.02 (1H, dd), 4.12 (0.5H, q, ethyl acetate), 4.50 (2H, d), 6.30 (1H, t), 6.74 (2H, dm), 7.00–7.19 (6H, m), 7.49 (2H, dm), 7.50 (2H, dm), COOH too broad to be observed.

Example 53

(Z)-(2S)-2-Ethoxy-3-{4-[3-(4-furan-2-yl-phenyl)-3-phenyl-allyloxy]-phenyl}-propionic acid ethyl ester Reaction of (Z)-3-(4-furan-2-yl-phenyl)-3-phenyl-prop-2-en-1-ol (300 mg, 1.09 mmol), tributylphosphine (0.40 ml, 1.64 mmol), (2S)-2-ethoxy-3-(4-hydroxy-phenyl)-propionic acid ethyl ester (286 mg, 1.20 mmol) and azodicarboxylic dipiperidide (413 mg, 1.64 mmol) in benzene in an identical manner to example 3 gave the title compound (260 mg, 48%).

¹H NMR (CDCl₃, 300 MHz); δ 1.15 (3H, t), 1.21 (3H, t), 2.93 (2H, d), 3.28–3.40 (1H, m), 3.52–3.65 (1H, m), 3.94 (1H, t), 4.14 (2H, q), 4.60 (2H, d), 6.30 (1H, t), 6.49 (1H, dd), 6.69 (1H, d), 6.77 (2H, dm), 7.11 (2H, dm), 7.18–7.32 (7H, m), 7.49 (1H, d), 7.69 (2H, dm).

LCMS (electrospray): 519 (M+Na), 514 (M+NH₄), 259 (100%).

Example 54

(Z)-(2S)-2-Ethoxy-3-{4-[3-(4-furan-2-yl-phenyl)-3-phenyl-allyloxy]-phenyl}-propionic acid (Z)-(2S)-2-Ethoxy-3-{4-[3-(4-furan-2-yl-phenyl)-3-phenyl-allyloxy]-phenyl}-propionic acid ethyl ester (example 53) (240 mg, 0.483 mmol) was hydrolyzed in an identical manner to example 2 to give the title compound (170 mg, 75%).

¹H NMR (CDCl₃, 300 MHz); δ 1.15 (3H, t), 2.93 (1H, dd), 3.05 (1H, dd), 3.33–3.49 (1H, m), 3.50–3.65 (1H, m), 4.01 (1H, dd), 4.60 (2H, d), 6.30 (1H, t), 6.49 (1H, dd), 6.68 (1H, d), 6.78 (2H, dm), 7.11 (2H, dm), 7.15–7.36 (7H, m), 7.49 (1H, d), 7.68 (2H, dm), COOH too broad to be observed.

LCMS (electrospray): 491 (M+Na), 486 (M+NH₄), 259 (100%).

Example 55

(E)-(2S)-3-{4-[3-(4-Bromophenyl)-3-phenyl-allyloxy]-phenyl}-2-ethoxy-propionic acid ethyl ester Reaction of (E)-3-(4-bromophenyl)-3-phenyl-prop-2-en-1-ol (289 mg, 1.0 mmol), tributylphosphine (0.37 ml, 1.5 mmol), (2S)-2-ethoxy-3-(4-hydroxy-phenyl)-propionic acid ethyl ester (262 mg, 1.10 mmol) and azodicarboxylic dipiperidide (378 mg, 1.5 mmol) in benzene in an identical manner to example 3 gave the title compound (460 mg, 90%).

¹H NMR (CDCl₃, 300 MHz); δ 1.15 (3H, t), 1.21 (3H, t), 2.92 (2H, d), 3.26–3.40 (1H, m), 3.51–3.65 (1H, m), 3.94 (1H, t), 4.15 (2H, q), 4.54 (2H, d), 6.29 (1H, t), 6.74 (2H, dm), 7.03–7.45 (11H, m).

LCMS (electrospray): 531/533 (M+Na), 271/273 (100%).

Example 56

(E)-(2S)-3-{4-[3-(4-Bromophenyl)-3-phenyl-allyloxy]-phenyl}-2-ethoxy-propionic acid (E)-(2S)-3-{4-[3-(4-Bromophenyl)-3-phenyl-allyloxy]-phenyl}-2-ethoxy-propionic acid ethyl ester (example 55) (382 mg, 0.75 mmol) was hydrolyzed in an identical manner to example 2 to give the title compound (350 mg, 97%).

¹H NMR (CDCl₃, 300 MHz); δ 1.16 (3H, t), 2.93 (1H, dd), 3.05 (1H, dd), 3.38–3.50 (1H, m), 3.50–3.63 (1H, m), 4.03 (1H, dd), 4.53 (2H, d), 6.30 (1H, t), 6.75 (2H, dm), 7.03–7.45 (11H, m), COOH too broad to be observed.

LCMS (electrospray): 503/505 (M+Na), 498/500 (M+NH₄), 271/273 (100%).

Example 57

(2S)-3-{4-[3,3-Bis-(4-furan-2-yl-phenyl)-allyloxy]-phenyl}-2-ethoxy-propionic acid ethyl ester Reaction of 3,3-bis-(4-furan-2-yl-phenyl)-prop-2-en-1-ol (460 mg, 1.34 mmol), tributylphosphine (0.50 ml, 2.0 mmol), (2S)-2-ethoxy-3-(4-hydroxy-phenyl)-propionic acid ethyl ester (320 mg, 1.34 mmol) and azodicarboxylic dipiperidide (504 mg, 2.0 mmol) in benzene in an identical manner to example 3 gave the title compound (541 mg, 72%).

¹H NMR (CDCl₃, 300 MHz); δ 1.16 (3H, t), 1.21 (3H, t), 2.93 (2H, d), 3.28–3.40 (1H, m), 3.51–3.64 (1H, m), 3.94 (1H, t), 4.14 (2H, q), 4.59 (2H, d), 6.35 (1H, t), 6.40–6.51 (2H, m), 6.62 (1H, d), 6.69 (1H, d), 6.77 (2H, dm), 7.13 (2H, dm), 7.20–7.33 (4H, m), 7.44 (1H, d), 7.48 (1H, d), 7.58 (2H, dm), 7.70 (2H, m).

Example 58

(2S)-3-{4-[3,3-Bis-(4-furan-2-yl-phenyl)-allyloxy]-phenyl}-2-ethoxy-propionic acid (2S)-3-{4-[3,3-Bis-(4-furan-2-yl-phenyl)-allyloxy]-phenyl}-2-ethoxy-propionic acid ethyl ester (example 57) (530 mg, 0.95 mmol) was hydrolyzed in an identical manner to example 2 to give the title compound (400 mg, 79%).

¹H NMR (CDCl₃, 300 MHz); δ 1.17 (3H, t), 2.95 (1H, dd), 3.07 (1H, dd), 3.40–3.52 (1H, m), 3.52–3.63 (1H, m), 4.05 (1H, dd), 4.60 (2H, d), 6.35 (1H, t), 6.44–6.51 (2H, m), 6.64 (1H, d), 6.70 (1H, d), 6.79 (2H, dm), 7.12 (2H, dm), 7.20–7.34 (4H, m), 7.47 (1H, d), 7.50 (1H, d), 7.59 (2H, dm), 7.70 (2H, dm), COOH too broad to be observed.

Example 59

(E, Z)-(2S)-3-[4-(3-Biphenyl-4-yl-3-p-tolyl-allyloxy)-phenyl]-2-ethoxy-propionic acid ethyl ester Reaction of (E, Z)-3-biphenyl-4-yl-3-p-tolyl-prop-2-en-1-ol (300 mg, 1.0 mmol), tributylphosphine (0.37 ml, 1.5 mmol), (2S)-2-ethoxy-3-(4-hydroxy-phenyl)-propionic acid ethyl ester (262 mg, 1.10 mmol) and azodicarboxylic dipiperidide (378 mg, 1.50 mmol) in benzene in an identical manner to example 3 gave the title compound (390 mg, 76%).

¹H NMR (CDCl₃, 300 MHz); δ 1.10–1.25 (6H, m), 2.30–2.42 (3H, m), 2.92 (2H, d), 3.27–3.40 (1H, m), 3.50–3.65 (1H, m), 3.94 (1H, tm), 4.13 (2H, qm), 4.57–4.64 (2H, m), 6.23–6.38 (1H, m), 6.79 (2H, dm), 7.03–7.67 (15H, dm).

LCMS (electrospray): 543 (M+Na), 538 (M+NH₄), 283 (100%).

Example 60

(E, Z)-(2S)-3-[4-(3-Biphenyl-4-yl-3-p-tolyl-allyloxy)-phenyl]-2-ethoxy-propionic acid (E, Z)-(2S)-3-[4-(3-Biphenyl-4-yl-3-p-tolyl-allyloxy)-phenyl]-2-ethoxy-propionic acid ethyl ester (example 59) (370 mg, 0.71 mmol) was hydrolyzed in an identical manner to example 2 to give the title compound (310 mg, 89%).

¹H NMR (CDCl₃, 300 MHz); δ 1.10–1.22 (3H, m), 2.30–2.44 (3H, m), 2.93 (1H, dd), 3.04 (1H, dd), 3.37–3.63

(2H, m), 3.98–4.07 (1H, m), 4.54–4.65 (2H, m), 6.25–6.38 (1H, m), 6.79 (2H, dm), 7.02–7.67 (15H, m), COOH too broad to be observed.

LCMS (electrospray): 515 (M+Na), 283 (100%).

Example 61

(E, Z)-(2R)-3-[4-(3-Biphenyl-4-yl-3-phenyl-allyloxy)-phenyl]-2-ethoxy-propionic acid ethyl ester Potassium carbonate (0.25 g, 1.81 mmol) was added to a stirred solution of 4-(3-bromo-1-phenyl-prop-1-enyl)-biphenyl (0.35 g, 1.00 mmol) and (2R)-2-ethoxy-3-(4-hydroxyphenyl)propionic acid ethyl ester (0.215 g, 0.90 mmol) in dry acetone (20 ml), and the mixture heated to 60° C. under reflux for 18 h. The resulting suspension was cooled to room temperature, filtered to remove inorganic products, and the solvents evaporated. The product was purified by flash column chromatography on silica gel, eluting with 15% ethyl acetate in light petroleum, to give the title compound as a colorless gum (0.40 g, 87%).

$^1$H NMR (CDCl$_3$, 300 MHz); δ 1.09–1.32 (6H, m), 2.93 (2H, d), 3.27–3.41 (1H, m), 3.51–3.67 (1H, m), 3.96 (1H, t), 4.18–4.20 (2H, m), 4.52–4.68 (2H, m), 6.28–6.41 (1H, r), 6.72–6.83 (2H, m), 7.12 (2H, dm), 7.18–7.69 (14H, m).

What is claimed is:

1. A compound of formula (I)

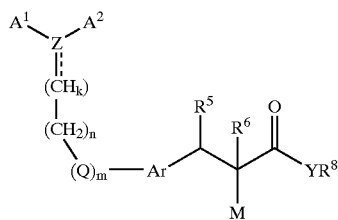

(I)

wherein $A^1$ and $A^2$ are independently of each other a saturated, unsaturated or aromatic 5–6 membered cyclic ring system selected from the group consisting of cyclopentyl, cyclohexyl, phenyl, thienyl, furanyl, pyridinyl wherein said ring system is optionally substituted with one or more halogen, perhalomethyl, hydroxy, $C_{1-6}$-alkyl, $(C_{3-6}$-cycloalkyl)$C_{1-6}$-alkyl, $C_{4-6}$-alkenynyl, $C_{2-6}$-alkenyl, $C_{2-6}$-alkynyl, $C_{1-6}$-alkoxy, aryl, aryloxy, arylalkyl, arylalkoxy, heteroaryl, heteroarylalkyl, heteroaryloxy, heteroarylalkoxy, acyl, hydroxy$C_{1-6}$-alkyl, $C_{1-6}$-alkyl-amino, $C_{1-6}$-dialkylamino, arylamino, arylalkylamino, amino$C_{1-6}$-alkyl, $C_{1-6}$-alkoxy$C_{1-6}$-alkyl, aryloxy$C_{1-6}$-alkyl, or arylalkoxy$C_{1-6}$-alkyl, wherein heteroaryl is selected from the group consisting of furanyl, thionyl and pyridinyl;

aryl is selected from the group consisting of phenyl and naphthyl;

heteroaryloxy is a heteroaryl group linked to an oxygen atom, wherein said heteroaryl is selected from the group consisting of furanyl, thienyl and pyridinyl;

heteroarylalkoxy is a heteroarylalkyl group linked to an oxygen atom, wherein said heteroarylalkyl is a straight or branched saturated carbon chain containing from 1 to 6 carbons substituted with a heteroaryl group, wherein said heteroaryl is selected from the group consisting of furanyl, thienyl and pyridinyl Z is C;

Q is O or S;

----- represents a single bond or a double bond;

Ar is arylene or heteroarylene, wherein arylene is a divalent aromatic ring, selected from the group consisting of phenylene and naphthylene; heteroarylene is a divalent heteroaryl group selected from the group consisting of furanyl, thienyl and pyridinyl;

$R^5$ is hydrogen;

$R^6$ is hydrogen;

M is OR$^7$, where R$^7$ is hydrogen, $C_{1-12}$-alkyl, $C_{4-12}$-alkenynyl, $C_{2-12}$-alkenyl, $C_{2-12}$-alkynyl, aryl, arylalkyl, $C_{1-12}$-alkoxy$C_{1-12}$-alkyl, acyl, heteroaryl or heteroarylalkyl groups optionally substituted with one or more halogen, perhalomethyl, hydroxy, nitro or cyano or M is COYR$^8$;

R$^8$ is hydrogen, $C_{1-12}$-alkyl, $C_{4-12}$-alkenynyl, $C_{2-12}$-alkenyl, $C_{2-12}$-alkynyl;

Y is oxygen;

k is an integer from 1 to 2, n and m are 1;

wherein heteroaryl is selected from the group consisting of furanyl, thienyl and pyridinyl;

aryl is selected from the group consisting of phenyl and naphthyl;

arylalkyl is selected from the group consisting of benzyl, phenethyl, 3-phenylpropyl, 1-naphtylmethyl and 2-(1-naphthyl)ethyl;

heteroaryloxy is a heteroaryl group linked to an oxygen atom, wherein said heteroaryl is selected from the group consisting of furanyl, thienyl and pyridinyl;

heteroarylalkoxy is a heteroarylalkyl group linked to an oxygen atom, wherein said heteroarylalkyl is a straight or branched saturated carbon chain containing from 1 to 6 carbons substituted with a heteroaryl group, wherein said heteroaryl is selected from the group consisting of furanyl, thiophenyl and pyridinyl;

or a salt thereof with a pharmaceutically acceptable acid or base, or any optical isomer or mixture of optical isomers, or any tautomeric forms.

2. The compound of claim 1, wherein $A^1$ and $A^2$ are independently of each other optionally substituted with one or more halogen, $C_{1-6}$-alkyl, $C_{1-6}$-alkoxy, aryl or heteroaryl, wherein aryl is selected from the group consisting of phenyl and naphthyl and heteroaryl is selected from the group consisting of furanyl, thienyl and pyridinyl.

3. The compound of claim 1, wherein M is OR$^7$, where R$^7$ is hydrogen, $C_{1-6}$-alkyl, $C_{4-6}$-alkenynyl, $C_{2-6}$-alkenyl, $C_{2-6}$-alkynyl, aryl, arylalkyl, $C_{1-6}$-alkoxy$C_{1-6}$-alkyl, $C_{1-6}$-alkoxycarbonyl, aryloxycarbonyl, $C_{1-6}$-alkylaminocarbonyl, arylaminocarbonyl, acyl, heteroaryl or heteroarylalkyl groups optionally substituted with one or more halogen, perhalomethyl, hydroxy, nitro or cyano, wherein heteroaryl is selected from the group consisting of furanyl, thienyl and pyridinyl;

aryl is selected form the group consisting of phenyl and naphthyl;

arylalkyl is selected from the group consisting of benzyl, phenethyl, 3-phenylpropyl, 1-naphtylmethyl and 2-(naphthyl)ethyl;

heteroarylalkyl is a straight or branched saturated carbon chain containing from 1 to 6 carbons substituted with a heteroaryl group, wherein said heteroaryl is selected from furanyl, thienyl and pyridinyl.

4. The compound of claim 1, wherein M is OR$^7$, where R$^7$ is hydrogen, $C_{1-6}$-alkyl, $C_{4-6}$-alkenynyl, $C_{2-6}$-alkenyl, $C_{2-6}$-alkynyl, aryl, arylalkyl, $C_{1-6}$-alkoxy$C_{1-6}$-alkyl, heteroaryl or heteroarylalkyl groups optionally substituted with one or more halogen or perhalomethyl,
wherein heteroaryl is selected from the group consisting of furanyl, thienyl and pyridinyl;
aryl is selected from the group consisting of phenyl and naphthyl;
arylalkyl is selected from the group consisting of benzyl, phenethyl, 3-phenylpropyl, 1-naphtylmethyl, 2-(1-napthyl)ethyl;
heteroarylalkyl is a straight or branched saturated carbon chain containing from 1 to 6 carbons substituted with a heteroaryl group, wherein said heteroaryl is selected from the group consisting of furanyl, thienyl and pyridinyl.

5. The compound of claim 1, wherein M is $OR^7$, where $R^7$ is $C_{1-6}$-alkyl.

6. The compound of claim 1, wherein M is $OR^7$, where $R^7$ is ethyl.

7. The compound of claim 1, wherein $R^8$ is hydrogen or $C_{1-6}$-alkyl.

8. The compound of claim 1, wherein $R^8$ is hydrogen or ethyl.

9. A compound of claim 1 selected from the group consisting of:
2-Ethoxy-3-{4-[3-phenyl-3-(4-methylphenyl)-allyloxy]-phenyl}-propionic acid ethyl ester,
2-Ethoxy-3-{4-[3-phenyl-3-(4-methylphenyl)-allyloxy]-phenyl}-propionic acid,
3-{4-[3-(2-Chloro-phenyl)-3-phenyl-allyloxy]-phenyl}-2-ethoxy-propionic acid ethyl ester,
3-{4-[3-(2-Chloro-phenyl)-3-phenyl-allyloxy]-phenyl}-2-ethoxy-propionic acid,
3-{4-[3,3-Bis-(4-methoxy-phenyl)-allyloxy]-phenyl}-2-ethoxy-propionic acid ethyl ester,
3-{4-[3,3-Bis-(4-methoxy-phenyl)-allyloxy]-phenyl}-2-ethoxy-propionic acid,
3-{4-[3-Phenyl-3-(biphenyl-4-yl)-allyloxy]-phenyl}-2-ethoxy-propionic acid ethyl ester,
3-{4-[3-Phenyl-3-(biphenyl-4-yl)-allyloxy]-phenyl}-2-ethoxy-propionic acid,
2-Ethoxy-3-{4-[3-phenyl-3-(thiophen-2-yl)-allyloxy]-phenyl}-propionic acid ethyl ester,
2-Ethoxy-3-{4-[3-phenyl-3-(thiophen-2-yl)-allyloxy]-phenyl}-propionic acid,
2-Ethoxy-3-{4-[3-phenyl-3-(pyridin-2-yl)-allyloxy]-phenyl}-propionic acid ethyl ester,
2-Ethoxy-3-{4-[3-phenyl-3-(pyridin-2-yl)-allyloxy]-phenyl}-propionic acid,
3-[4-3,3-Diphenyl-propoxy)-phenyl]-2-ethoxy-propionic acid ethyl ester,
3-[4-3,3-Diphenyl-propoxy)-phenyl]-2-ethoxy-propionic acid,
2-Ethoxy-3-{4-[3-phenyl-3-(4-methylphenyl)-propoxy]-phenyl}-propionic acid ethyl ester,
2-Ethoxy-3-{4-[3-phenyl-3-(4-methylphenyl)-propoxy]-phenyl}-propionic acid,
3-{4-[3-Phenyl-3-(biphenyl-4-yl)-propoxy]-phenyl}-2-ethoxy-propionic acid ethyl ester,
3-{4-[3-Phenyl-3-(biphenyl-4-yl)-propoxy]-phenyl}-2-ethoxy-propionic acid,
2-{4-[3,3-Bis-(4-methoxy-phenyl)-allyloxy]-benzyl}-malonic acid dim ethyl ester,
(E)-(2S)-2-Ethoxy-3-{4-[3-(4-furan-2-yl-phenyl)-3-phenyl-allyloxy]-phenyl}-propionic acid ethyl ester,
(E)-(2S)-2-Ethoxy-3-{4-[3-(4-furan-2-yl-phenyl)-3-phenyl-allyloxy]-phenyl}-propionic acid,
(E)-(2S)-3-[4-(3-Biphenyl-4-yl-3-phenyl-allyloxy)-phenyl]-2-ethoxy-propionic acid ethyl ester,
(E)-(2S)-3-[4-(3-Biphenyl-4-yl-3-phenyl-allyloxy)-phenyl]-2-ethoxy-propionic acid,
(E, Z)-(2S)-3-[4-(3-Biphenyl-4-yl-3-phenyl-allyloxy)-phenyl]-2-ethoxy-propionic acid ethyl ester,
(E, Z)-(2S)-3-[4-(3-Biphenyl-4-yl-3-phenyl-allyloxy)-phenyl]-2-ethoxy-propionic acid,
3-{4-[3,3-Bis-(3-methyl-thiophen-2-yl)-allyloxy]-phenyl}-2-ethoxy-propionic acid ethyl ester,
3-{4-[3,3-Bis-(4-bromo-phenyl)-allyloxy]-phenyl}-2-ethoxy-propionic acid ethyl ester,
3-{4-[3,3-Bis-(4-bromo-phenyl)-allyloxy]-phenyl}-2-ethoxy-propionic acid,
2-Ethoxy-3-[4-(3-phenyl-3-pyridin-4-yl-allyloxy)-phenyl]-propionic acid ethyl ester,
2-Ethoxy-3-[4-(3-phenyl-3-pyridin-4-yl-allyloxy)-phenyl]-propionic acid,
(E, Z)-(2S)-2-Ethoxy-3-{4-[3-(4-methoxyphenyl)-3-thiophen-2-yl-allyloxy]-phenyl}-propionic acid ethyl ester,
(E, Z)-(2S)-2-Ethoxy-3-{4-[3-(4-methoxyphenyl)-3-thiophen-2-yl-allyloxy]-phenyl}-propionic acid,
(E, Z)-(2S)-2-Ethoxy-3-[4-(3-phenyl-3-p-tolyl-allyloxy)-phenyl]-propionic acid ethyl ester,
(E, Z)-(2S)-2-Ethoxy-3-[4-(3-phenyl-3-p-tolyl-allyloxy)-phenyl]-propionic acid,
(2S)-3-[4-(3,3-Diphenyl-allyloxy)-phenyl]-2-ethoxy-propionic acid ethyl ester,
(2S)-3-[4-(3,3-Diphenyl-allyloxy)-phenyl]-2-ethoxy-propionic acid,
(Z)-(2S)-2-Ethoxy-3-{4-[3-(4-fluorophenyl)-3-phenyl-allyloxy]-phenyl}-propionic acid ethyl ester,
(Z)-(2S)-2-Ethoxy-3-{4-[3-(4-fluorophenyl)-3-phenyl-allyloxy]-phenyl}-propionic acid,
(E)-(2S)-2-Ethoxy-3-{4-[3-(4-fluorophenyl)-3-phenyl-allyloxy]-phenyl}-propionic acid ethyl ester,
(E)-(2S)-2-Ethoxy-3-{4-[3-(4-fluorophenyl)-3-phenyl-allyloxy]-phenyl}-propionic acid,
(2S)-3-{4-[3,3-Bis-(4-methoxyphenyl)-allyloxy]-phenyl}-2-ethoxy-propionic acid ethyl ester,
(2S)-3-{4-[3,3-Bis-(4-methoxyphenyl)-allyloxy]-phenyl}-2-ethoxy-propionic acid,
(2S)-3-[4-(3,3-Di-p-tolyl-allyloxy)-phenyl]-2-ethoxy-propionic acid ethyl ester,
(2S)-3-[4-(3,3-Di-p-tolyl-allyloxy)-phenyl]-2-ethoxy-propionic acid,
(Z)-(2S)-3-[4-(3-Biphenyl-4-yl-3-phenyl-allyloxy)-phenyl]-2-ethoxy-propionic acid,
(Z)-(2S)-3-{4-[3-(4-Bromophenyl)-3-phenyl-allyloxy]-phenyl}-2-ethoxy-propionic acid ethyl ester,
(Z)-(2S)-3-{4-[3-(4-Bromophenyl)-3-phenyl-allyloxy]-phenyl}-2-ethoxy-propionic acid,
(2S)-3-[4-(3,3-Bis-biphenyl-4-yl-allyloxy)-phenyl]-2-ethoxy-propionic acid ethyl ester,
(2S)-3-[4-(3,3-Bis-biphenyl-4-yl-allyloxy)-phenyl]-2-ethoxy-propionic acid,
(2S)-3-{4-[3,3-Bis-(4-bromophenyl)-allyloxy]-phenyl}-2-ethoxy-propionic acid ethyl ester,
(2S)-3-{4-[3,3-Bis-(4-bromophenyl)-allyloxy]-phenyl}-2-ethoxy-propionic acid,
(Z)-(2S)-2-Ethoxy-3-{4-[3-(4-furan-2-yl-phenyl)-3-phenyl-allyloxy]-phenyl}-propionic acid ethyl ester,
(Z)-(2S)-2-Ethoxy-3-{4-[3-(4-furan-2-yl-phenyl)-3-phenyl-allyloxy]-phenyl}-propionic acid,
(E)-(2S)-3-{4-[3-(4-Bromophenyl)-3-phenyl-allyloxy]-phenyl}-2-ethoxy-propionic acid ethyl ester, (E)-(2S)-3-{4-[3-(4-Bromophenyl)-3-phenyl-allyloxy]-phenyl}-2-ethoxy-propionic acid, (2S)-3-{4-[3,3-Bis-(4-furan-2-yl-phenyl)-allyloxy]-phenyl}-2-ethoxy-propionic acid ethyl ester, (2S)-3-{4-[3,3-Bis-(4-furan-2-yl-phenyl)-allyloxy]-phenyl}-2-ethoxy-propionic acid, (E, Z)-(2S)-3-[4-(3-Biphenyl-4-yl-3-p-tolyl-allyloxy)-phenyl]-2-ethoxy-propionic acid ethyl ester, (E, Z)-(2S)-3-[4-(3-Biphenyl-4-yl-3-p-tolyl-allyloxy)-phenyl]-2-ethoxy-propionic acid, or (E, Z)-(2R)-3-[4-(3-Biphenyl-4-yl-3-p-tolyl-allyloxy)-phenyl]-2-ethoxy-propionic acid ethyl ester;

or a salt thereof with a pharmaceutically acceptable acid or base, or any optical isomer or mixture of optical isomers, or any tautomeric forms.

10. The compound of claim 9 which is (2S)-3-[4-(3,3-Bis-biphenyl-4-yl-allyloxy)-phenyl]-2-ethoxy-propionic acid ethyl ester, or (2S)-3-[4-(3,3-Bis-biphenyl-4-yl-allyloxy)-phenyl]-2-ethoxy-propionic acid, or a salt thereof with a pharmaceutically acceptable acid or base, or any optical isomer or mixture of optical isomers, or any tautomeric forms.

11. The compound of claim 9 which is (2S)-3-{4-[3,3-Bis-(4-bromophenyl)-allyloxy]-phenyl}-2-ethoxy-propionic acid ethyl ester, or (2S)-3-{4-[3,3-Bis-(4-bromophenyl)-allyloxy]-phenyl}-2-ethoxy-propionic acid, or a salt thereof with a pharmaceutically acceptable acid or base, or any optical isomer or mixture of optical isomers, or any tautomeric forms.

12. The compound of claim 9 which is (2S)-3-{4-[3,3-Bis-(4-furan-2-yl-phenyl)-allyloxy]-phenyl}-2-ethoxy-propionic acid ethyl ester, or (2S)-3-{4-[3,3-Bis-(4-furan-2-yl-phenyl)-allyloxy]-phenyl}-2-ethoxy-propionic acid, or a salt thereof with a pharmaceutically acceptable acid or base, or any optical isomer or mixture of optical isomers, or any tautomeric forms.

13. The compound according to claim 1, wherein heteroarylalkoxy is a heteroarylalkyl linked to an oxygen atom having its free valence bond from the oxygen atom, said heteroarylalkyl selected from the group consisting of (2-furyl)methyl, (3-furyl)methyl, (2-thienyl)methyl, (3-thienyl)methyl and (2-pyridyl)methyl.

14. A composition comprising, as an active ingredient, an effective amount of the compound of claim 1, together with a pharmaceutically acceptable carrier or diluent.

15. The composition of claim 14 in unit dosage form, comprising from about 0.05 to about 100 mg of the compound.

16. The composition of claim 14 in unit dosage form, comprising from about 0.1 to about 100 mg of the compound.

17. The composition of claim 14 which is administered by the oral, nasal, transdermal, pulmonary, or parenteral route.

* * * * *